United States Patent [19]

Hur et al.

[11] Patent Number: 5,494,888
[45] Date of Patent: Feb. 27, 1996

[54] 6-CHLORO-2-(4,6-DIMETHOXYPYRIMIDIN-2-YL)OXYBENZOIC ACID IMINO ESTER DERIVATIVES, PROCESSES FOR THEIR PRODUCTION AND A METHOD FOR THEIR APPLICATION AS HERBICIDES

[75] Inventors: Chang U. Hur; Jin H. Cho; Ho S. Lee; Sang K. Yoo; Su M. Hong; Hong W. Kim; Jae S. Rim; Yeong T. Bae; Sang H. Chae; Jeong S. Kim; Byoung B. Lee; Hun S. Oh; Woo B. Choi, all of Youseong-ku, Rep. of Korea

[73] Assignee: Lucky Ltd., Seoul, Rep. of Korea

[21] Appl. No.: 186,589

[22] Filed: Jan. 26, 1994

[30] Foreign Application Priority Data

| Jan. 27, 1993 | [KR] | Rep. of Korea | 93-1017 |
| Jun. 4, 1993 | [KR] | Rep. of Korea | 93-10097 |
| Jun. 4, 1993 | [KR] | Rep. of Korea | 93-10098 |
| Jun. 4, 1993 | [KR] | Rep. of Korea | 93-10099 |
| Jun. 4, 1993 | [KR] | Rep. of Korea | 93-10100 |
| Jun. 4, 1993 | [KR] | Rep. of Korea | 93-10101 |

[51] Int. Cl.$^6$ .................. A01N 43/54; C07D 239/60; C07D 413/00
[52] U.S. Cl. .................. 504/243; 504/225; 544/123; 544/299; 544/300; 544/301
[58] Field of Search .................. 544/299, 300, 544/301, 123; 504/243, 225

[56] References Cited

U.S. PATENT DOCUMENTS

| 4,889,552 | 12/1989 | Wada et al. | 544/299 |
| 4,900,352 | 2/1990 | Wada et al. | 544/299 |
| 4,923,501 | 5/1990 | Saito et al. | 544/299 |
| 5,019,151 | 5/1991 | Wada et al. | 544/299 |
| 5,053,070 | 10/1991 | Gohbara et al. | 544/299 |
| 5,055,471 | 10/1991 | de Fraine et al. | 544/299 |
| 5,232,897 | 8/1993 | Hiratsuka et al. | 544/299 |

FOREIGN PATENT DOCUMENTS

| 0223406 | 5/1987 | European Pat. Off. |
| 0287072 | 10/1988 | European Pat. Off. |
| 0287079 | 10/1988 | European Pat. Off. |
| 0315889 | 5/1989 | European Pat. Off. |
| 0321846 | 6/1989 | European Pat. Off. |
| 0330990 | 9/1989 | European Pat. Off. |
| 0335409 | 10/1989 | European Pat. Off. |
| 0346789 | 12/1989 | European Pat. Off. |
| 0363040 | 4/1990 | European Pat. Off. |
| 0435170 | 7/1991 | European Pat. Off. |
| 0435186 | 7/1991 | European Pat. Off. |
| 0457505 | 11/1991 | European Pat. Off. |
| 3942476 | 6/1991 | Germany. |
| 2237570 | 5/1991 | United Kingdom. |

OTHER PUBLICATIONS

Peter Babczinski et al., Pestic. Sci., "Mode of Action of Herbicidal ALS–Inhibitors on Acetolactate Synthase from Green Plant Cell Cultures, Yeast, and *Escherichia coli*" vol. 30, No. 3, pp. 305–323 (1991).

Edwin M. Kaiser et al, The Journal of Organic Chemistry, "Synthesis of Esters of Acid–Unstable Alcohols by Means of n–Butyllithium," vol. 35, No. 4, pp. 1198–1199 (1970).

Teruomi Jojima et al., Agr. Biol. Chem., vol. 30, No. 9, pp. 896–905 (1966).

*Primary Examiner*—Cecilia Tsang
*Attorney, Agent, or Firm*—Willian Brinks Hofer Gilson & Lione

[57] ABSTRACT

The present invention relates to 6-chloro-2-(4,6-dimethoxypyrimidin-2-yl)oxybenzoic acid iminoester derivative of the general formula I; process of their preparation and a method for their application as herbicides:

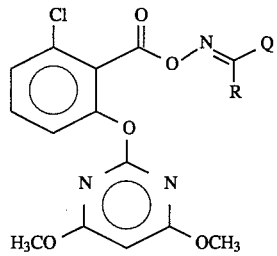

wherein R and Q are as defined in the specification.

14 Claims, No Drawings

6-CHLORO-2-(4,6-DIMETHOXYPYRIMIDIN-2-YL)OXYBENZOIC ACID IMINO ESTER DERIVATIVES, PROCESSES FOR THEIR PRODUCTION AND A METHOD FOR THEIR APPLICATION AS HERBICIDES

FIELD OF THE INVENTION

The present invention relates to novel herbicidal pyrimidine derivatives; And, more particularly, novel 6-chloro-2-(4,6-dimethoxypyrimidin-2-yl)oxybenzoic acid imino ester derivatives, the processes for preparing thereof, herbicidal compositions containing the compounds as active ingredients and a method for their application as herbicides to agricultural fields. The invention also relates to novel intermediates thereof.

BACKGROUND OF THE INVENTION

It is widely disclosed that 2-phenoxypyrimidine, or (pyrimidin-2-yl) oxybenzene derivatives are useful as herbicides, for instance, in Arg. Biol. Chem., Vol. 30, No. 9, p. 896 (1966), and Japanese Unexamined Patent Publication No. 55729/1979 and so on. Among 2-phenoxypyrimidine compounds developed in recent years, particularly, some 2-(pyrimidin-2-yl)oxybenzoic acid derivatives have invited great attention in the art because of their potent herbicidal activities.

In the prior art, as 2-(pyrimidin-2-yl)oxybenzoic acid derivatives, there have been known a large number of compounds, as disclosed in European Patent Publication No. 223,406, No. 249,708, No. 287,072, No. 287,079, No. 315,889, No. 321,846, No. 330,990, No. 335,409, No. 346,789, No. 363,040, No. 435,170, No. 435,186, No. 457,505; GB Patent Publication No. 2,237,570; DE Patent Publication No. 3,942,476 and so on.

These compounds in above mentioned publications show herbicidal mode of action similar to that of sulfonyl ureas, imidazolinones and triazolopyrimidines well-known as typical amino acid biosynthesis inhibitory herbicides, and also have merits of being easily prepared with their simple structures.

From the investigation on the herbicidal mode of action, it was revealed that the above known compounds impair the activity of ALS, i.e., Acetolactate Synthase; and which is known to involve in the procedure of synthesizing Acetolactate at the first stage of the biosynthesis pathway of essential amino acid, valine, isoleucine, etc., from pyruvic acid in plant body.

In this connection, it was reported on the study of enzyme activity assay using ALS by Peter B. et al., that 2-(pyrimidin-2-yl)oxybenzoic acid esters are pro-herbicides which have no herbicidal activities in themselves, and are only active after hydrolysis with carboxylesterase in plant body to their free acid forms [Peter B. et al., Pestic. Sci., Vol. 30, No. 3, p 305–324 (1991)].

SUMMARY OF THE INVENTION

The present inventors, however, have put much effort into the extensive research on 2-(pyrimidin-2-yl)oxybenzoic acid ester derivatives for new chemical classes of ALS inhibitory herbicides, and as a result, have found that certain specific types of these compounds, contrary to previous mentioned Peter's report, have their own excellent activities of ALS inhibitors. Moreover, it was surprising that some imino esters of 2-(pyrimidin-2-yl)oxybenzoic acid have superior herbicidal effects. That is, the imino ester-type compounds of this invention are not pre-herbicides but excellent herbicidal ALS inhibitors in themselves, and exhibit markedly higher herbicidal activities as compared with aforementioned known compounds, at a relatively low dose not only against annual weeds but also against perennial weeds, and at the same time, they have a high level of safety for crop plants such as cotton (*Gossypium hirsutum*), rice plant (*Oryza sativa*), wheat (*Triticum aestivum*) or soybean (*Glycine max*), and are effective not only the major weeds grown such crop plant fields but also against generally hardly controllable weeds. The compounds of the present invention have a feature that their toxicity against human beings and animals is very low while their herbicidal activities are very high. The present invention has been accomplished on the basis of these findings.

Thus, it is the primary object of the present invention to provide novel 6-chloro-2-(4,6-dimethoxypyrimidin-2-yl)oxybenzoic acid imino ester derivatives having a high inhibitory effect against ALS, useful for controlling weeds in crop plant fields.

Another object of the present invention is to provide novel compounds useful as intermediates for preparing the compounds.

A further object of the present invention is to provide processes for preparing said compounds and intermediates thereof.

A still further object of the present invention is to provide herbicidal compositions containing the same in a herbicidally effective amount as active ingredients, and agriculturally suitable adjuvants.

Finally, the other object of the present invention is to provide a method for killing weeds which comprises applying a herbicidally effective amount of a 6-chloro-2-(4,6-dimethoxypyrimidin-2-yl)oxybenzoic acid imino esters to an area to be protected.

DETAILED DESCRIPTION OF THE INVENTION

In accordance with the invention, there are provided novel 6-chloro-2-(4,6-dimethoxypyrimidin-2-yl)oxybenzoic acid imino ester derivatives of the general formula (I):

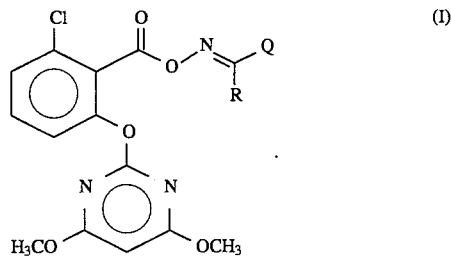

Wherein,

Q represents a straight or branched alkyl, alkenyl or cycloalkyl group having from 1 to 10 carbon atoms, preferably from 1 to 8 carbon atoms, which may be substituted with a $(C_1-C_4)$alkoxy or $(C_1-C_4)$alkylthio group; a $(C_1-C_4)$alkyl or $(C_2-C_4)$alkenylthio group; a phenylthio group; a phenyl$(C_1-C_4)$alkyl or phenyl$(C_2-C_4)$alkenylthio group; or a radical of the following formula:

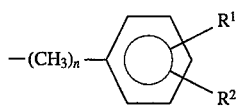

wherein $R^1$ and $R^2$ are same or different each other and represent hydrogen or a halogen atom; or a group selected from the groups which comprises with a $(C_1-C_4)$alkyl, a $(C_2-C_4)$alkenyl, an acyl, an acyloxy, a $(C_1-C_4)$alkylthio, a nitro, a cyano, an phenyl and a phenoxy group, and which, if necessary, may be substituted with a halogen atom, a $(C_1-C_4)$alkyl, a $(C_a-C_4)$alkoxy or an acetal group; or $R^1$ and $R^2$ may constitute an acetal structure with carbon atoms to which $R^1$ and $R^2$ are linked; and, n is 0 or 1; or a 5–6 membered ring system containing one or more hetero atoms such as oxygen, sulfur or nitrogen atom in the ring system, which may have one or more proper substituents such as a halogen atom, a $(C_1-C_4)$alkyl, a hydroxy, a nitro or a cyano group on its certain positions; and, R represents a hydrogen or a halogen atom, a cyano group, or $-Z-R^3$ wherein, $R^3$ represents a $(C_1-C_4)$alkyl, an alkoxy or alkenyloxy group having from 1 to 8 carbon atoms, or a phenyl, a phenoxy or an amino group, or 5–6 membered hetero or aromatic ring system connecting to Z through out a $(C_1-C_2)$alkyl or alkoxy bridge, such as a phenyl, a furyl, a thienyl, pyrrolyl or pyranyl group, and which may have one or more proper substituents such as a halogen atom, a $(C_1-C_4)$alkyl, a hydroxy, a nitro or a cyano group on its certain positions, or $R^3$ may be cyclized with Z and Q in some cases; and, Z represents —O—, —S—,

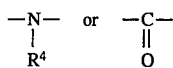

wherein, $R^4$ is a hydrogen atom, a $(C_1-C_4)$alkyl or a phenyl group, or constitutes a cyclic system containing an oxygen atom with $R^3$.

Among the compounds of formula (I) according to this invention, there may be syn-isomer or anti-isomer separately with respect to imino group, or mixtures of syn- and anti-isomers, and these isomers also belong to the scope of the invention.

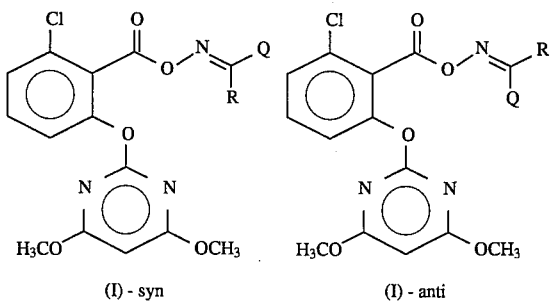

wherein,

R and Q are as defined above.

In this specification, the term "alkyl group", unless there is specific restriction, means an alkyl group having 1 to 10 carbon atoms, which may be saturated or unsaturated hydrocarbons, and also be a straight chain, branched or cycloalkyl group.

The term, "hetero ring" means a 5–6 membered mono or bicyclic ring containing one or more hetero atoms such as oxygen, nitrogen or sulfur atom in the ring system, which may also have single, double or/and triple bonds.

In a preferred embodiment, "alkyl group" may include, for example, methyl, ethyl, n-propyl, i-propyl, n-butyl, i-butyl, t-butyl, n-pentyl, i-pentyl, n-hexyl, i-hexyl, n-heptyl or n-octyl.

"Alkenyl group" may desirably include such as vinyl, allyl, 1-propenyl or 2,4-butadienyl.

The preferred embodiment of "cycloalkyl" may include cyclopropyl, cyclopentyl or cyclohexyl.

The preferred embodiment of "alkoxy/akenyloxy group" may include, for example methoxy, ethoxy, n-propoxy, i-propoxy, n-butoxy, sec-butoxy, t-butoxy, i-butoxy, allyloxy, pentyloxy, n-hexyloxy, i-hexyloxy, cyclohexyloxy or octyloxy.

It is preferred that "lower alkoxyalkyl group" may include, for example, methoxymethyl or ethoxyethyl.

In a preferred embodiment, "lower haloalkyl group" may include, for example, trifluoromethyl group.

In a preferred embodiment, "acyl group" may include, for example, acetyl; and "acetal group" may be, for example, 3,4-methylenedioxyphenyl or 1,1-ethylenedioxyethyl.

In a preferred embodiment, "substituted amino group" may include, for example, dimethylamino, diethylamino, i-propylamino or t-butylamino.

"Amine derivative" may be preferably, for example, methoxycarbonyl methylamino, ethoxycarbonylmethylamino, 1-methoxycarbonyl-2-phenylethyl amino, 1,1-di(ethoxycarbonyl)methylamino, 1,2-di(methoxycarbonyl)ethyl amino or 2-carbamoyl-3-methylbutan-2-ylamino.

"Alkyl/alkenylthio group" may be preferably, for example, methylthio, ethylthio, propylthio, i-propylthio, allylthio, n-butylthio, sec-butylthio or i-butylthio group.

And, "hetero ring" may desirably include, for example, 2-pyridinyl, 2-furyl, 2-nitro-5-furyl, benzo-2-furyl, 2-methyl-5-furyl, 2,5-dimethyl-3-furyl, 2- or 3-thienyl, 2-chlorothienyl, 3-methyl-2-thienyl, 2-methyl- 5-thienyl, 2-ethyl-4-methyl-5-thienyl, 2-nitro-5-thienyl or N-methyl-3-pyrrolyl group.

Now, specific examples of the compounds (I) of the present invention will be presented in Table 1. Compound numbers and symbols of substituentes as given in the Table will be referred to in the subsequent description in the specification.

TABLE 1

(I-a)

| Compound No. | Q | $R^3$ |
|---|---|---|
| 1 | $CH_3$ | $CH_3O$ |
| 2 | $CH_3$ | $C_2H_5O$ |
| 3 | $CH_3$ | $n-C_3H_7O$ |
| 4 | $CH_3$ | $i-C_3H_7O$ |
| 5 | $CH_3$ | $CH_2=CHCH_2O$ |

TABLE 1-continued

| | | |
|---|---|---|
| 6 | CH₃ | n-C₄H₉O |
| 7 | CH₃ | n-C₈H₁₇O |
| 8 | CH₃ | 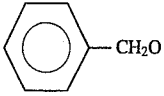—CH₂O |
| 9 | C₂H₅ | C₂H₅O |
| 10 | n-C₃H₇ | CH₃O |
| 11 | n-C₃H₇ | C₂H₅O |
| 12 | i-C₃H₇ | CH₃O |
| 13 | i-C₃H₇ | C₂H₅O |
| 14 | CH₂=CHCH₂ | C₂H₅O |
| 15 | n-C₄H₉ | CH₃O |
| 16 | n-C₄H₉ | C₂H₅O |
| 17 | n-C₄H₉ | n-C₃H₇O |
| 18 | i-C₄H₉ | CH₃O |
| 19 | i-C₄H₉ | C₂H₅O |
| 20 | 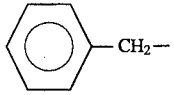—CH₂— | C₂H₅O |
| 21 | i-C₅H₁₁ | C₂H₅O |
| 22 | 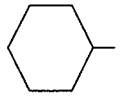 | C₂H₅O |
| 23 | n-C₅H₁₁ | C₂H₅O |
| 24 | n-C₈H₁₇ | C₂H₅O |
| 25 | sec-C₄H₉ | C₂H₅O |
| 26 | n-C₄H₉ (CH₃S)CH | C₂H₅O |
| 27 | C₂H₅OCH₂CH₂ | C₂H₅O |
| 28 | CH₃ | CH₃ |
| 29 |  | CH₃O |
| 30 |  | C₂H₅O |
| 31 |  | n-C₃H₇O |
| 32 |  | i-C₃H₇O |
| 33 |  | CH₂=CHCH₂O |
| 34 |  | 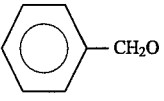—CH₂O |
| 35 |  | 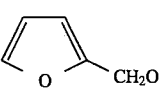—CH₂O |
| 36 | 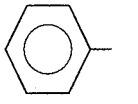 | 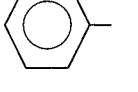—CH₂O |
| 37 |  | 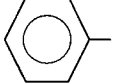—CH₂O |
| 38 | 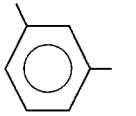 | CH₃O |
| 39 | 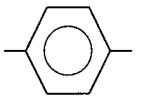 | CH₃O |
| 40 | 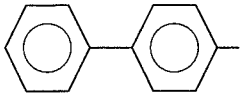 | C₂H₅O |
| 41 | 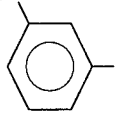 | CH₃O |
| 42 | 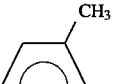 | CH₃O |
| 43 | 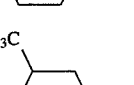 | CH₃O |
| 44 | 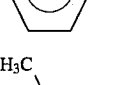 | CH₃O |
| 45 |  | C₂H₅O |
| 46 |  | CH₃O |
| 47 |  | CH₃O |

TABLE 1-continued

| 48 | 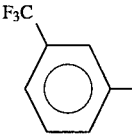 F$_3$C— (phenyl) | CH$_3$O |
| 49 | 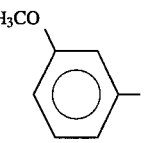 H$_3$CO— (phenyl) | CH$_3$O |
| 50 | 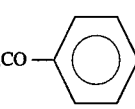 H$_3$CO— (phenyl) | CH$_3$O |
| 51 | 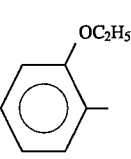 OC$_2$H$_5$ (phenyl) | CH$_3$O |
| 52 | 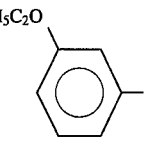 H$_5$C$_2$O— (phenyl) | CH$_3$O |
| 53 | 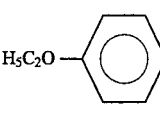 H$_5$C$_2$O— (phenyl) | CH$_3$O |
| 54 | 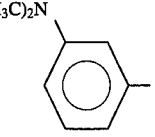 (H$_3$C)$_2$N— (phenyl) | CH$_3$O |
| 55 | 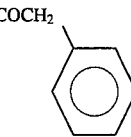 H$_3$COCH$_2$— (phenyl) | CH$_3$O |
| 56 | 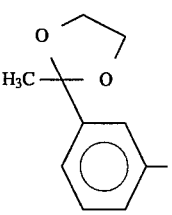 dioxolanyl-phenyl | CH$_3$O |
| 57 | 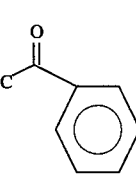 H$_3$C-CO— (phenyl) | CH$_3$O |
| 58 | CH$_3$O | —NH$_2$CHCO$_2$CH$_3$<br>    |<br>    CH$_2$—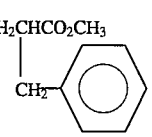 |
| 59 | 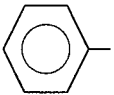 (phenyl) | —N(CH$_3$)$_2$ |
| 60 | 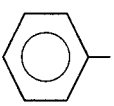 (phenyl) | —NHCH$_2$CO$_2$C$_2$H$_5$ |
| 61 | 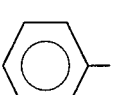 (phenyl) | —NHCH(CO$_2$C$_2$H$_4$)$_2$ |
| 62 | 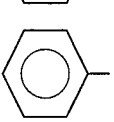 (phenyl) | —NHCHCO$_2$CH$_3$<br>    |<br>    CH$_2$CO$_2$CH$_3$ |
| 63 | 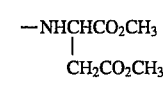 (phenyl) | CH$_3$<br>    |<br>—NHCHCONH$_2$<br>    |<br>    CH(CH$_3$)$_2$ |

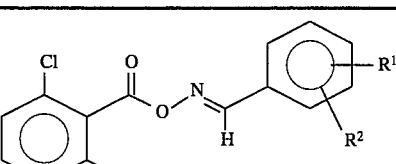

(I-b)

| Compound No. | R$^1$ | R$^2$ |
|---|---|---|
| 64 | H | H |
| 65 | 2'-, CH$_3$ | H |
| 66 | 3'-, CH$_3$ | H |
| 67 | 4'-, CH$_3$ | H |
| 68 | 4'-, C$_2$H$_5$ | H |
| 69 | 4'-, i-C$_3$H$_7$ | H |
| 70 | 4'-, Cl | H |
| 71 | 3'-, Cl | H |
| 72 | 2'-, F | H |
| 73 | 3'-, F | H |
| 74 | 4'-, F | H |
| 75 | 4'-, CH$_3$O | H |
| 76 | 3'-, CH$_3$O | H |
| 77 | 4'-, C$_2$H$_5$ | H |
| 78 | 2'-, C$_2$H$_5$ | H |
| 79 | 4'-, Phenoxy | H |
| 80 | 4'-, Butoxy | H |
| 81 | 3'-, Benzyloxy | H |
| 82 | 4'-, Benzyloxy | H |
| 83 | 4'-, Acetoxy | H |
| 84 | 4'-, F$_3$CO | H |
| 85 | 4'-, NO$_2$ | H |
| 86 | 4'-, (CH$_3$)$_2$N | H |
| 87 | 2'-, CF$_3$ | H |
| 88 | 3'-, CF$_3$ | H |
| 89 | 4'-, CF$_3$ | H |
| 90 | 4'-, Methoxycarbonyl | H |
| 91 | 4'-, CH$_3$S | H |
| 92 | 4'-, CN | H |
| 93 | 3'-, Cl | 5'-, Cl |
| 94 | 2'-, CH$_3$O | 5'-, Br |
| 95 | 2'-, F | 6'-, Cl |
| 96 | 3'-, F | 5'-, F |
| 97 | 2'-, Cl | 3'-, Cl |
| 98 | 2'-, Cl | 4'-, Cl |

TABLE 1-continued

| | | |
|---|---|---|
| 99 | 3'-, Cl | 4'-, Cl |
| 100 | 2'-, Cl | 5'-, NO$_2$ |
| 101 | 2'-, CH$_3$O | 3'-, CH$_3$O |
| 102 | 3'-, CH$_3$O | 5'-, CH$_3$O |
| 103 | 2'-, CH$_3$O | 4'-, CH$_3$O |
| 104 | 3'-, CH$_3$O | 5'-, CH$_3$O |
| 105 | 3'-, CH$_3$O | 4'-, Acetoxy |
| 106 | 3',4'-Methylenedioxy | |

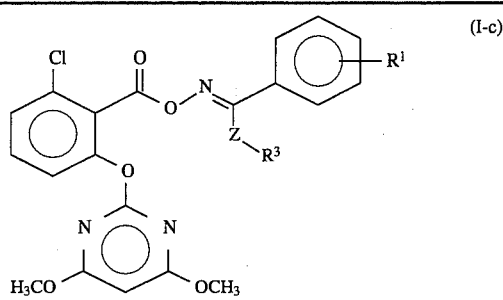 (I-c)

| Compound No | R$^1$ | R$^3$ | Z | Isomerism (ratio) |
|---|---|---|---|---|
| 107 | H | CH$_3$ | O | syn |
| 108 | H | C$_2$H$_5$ | O | syn |
| 109 | H | n-C$_3$H$_7$ | O | syn |
| 110 | 2'-, CH$_3$ | CH$_3$ | O | syn + anti (1:1) |
| 111 | 3'-, CH$_3$ | CH$_3$ | O | syn + anti (3:1) |
| 112 | 4'-, CH$_3$ | CH$_3$ | O | syn + anti (1:1) |
| 113 | 4'-, C$_2$H$_5$ | CH$_3$ | O | syn |
| 114 | 4'-, CH$_3$O | CH$_3$ | O | syn |
| 115 | 3'-, Cl | CH$_3$ | O | syn + anti (1:1) |
| 116 | 4'-, Cl | CH$_3$ | O | syn |
| 117 | 4'-, F | CH$_3$ | O | syn |
| 118 | 4'-, CH$_3$ | C$_2$H$_5$ | O | syn |
| 119 | 4'-, CH$_3$O | C$_2$H$_5$ | O | syn |
| 120 | 4'-, CH$_3$S | CH$_3$ | O | syn |
| 121 | 4'-, CN | CH$_3$ | O | syn |
| 122 | 4'-, CF$_3$ | CH$_3$ | O | syn |
| 123 | 4'-, (CH$_3$)$_2$N | CH$_3$ | O | syn |
| 124 | H | CH$_3$ | S | syn |
| 125 | H | C$_2$H$_5$ | S | syn |
| 126 | H | Phenyl | S | syn |
| 127 | 2'-, CH$_3$ | CH$_3$ | S | syn |
| 128 | 3'-, CH$_3$ | CH$_3$ | S | syn |
| 129 | 4'-, CH$_3$ | CH$_3$ | S | syn |
| 130 | 4'-, C$_2$H$_5$ | CH$_3$ | S | syn |
| 131 | 4'-, n-C$_3$H$_7$ | CH$_3$ | S | syn |
| 132 | 4'-, CF$_3$ | CH$_3$ | S | syn |
| 133 | 3'-, CH$_3$O | CH$_3$ | S | syn + anti (5:1) |
| 134 | 4'-, CH$_3$O | CH$_3$ | S | syn |
| 135 | 4'-, CN | CH$_3$ | S | syn |
| 136 | 3'-, Cl | CH$_3$ | S | syn |
| 137 | 4'-, Cl | CH$_3$ | S | syn |
| 138 | 4'-, F | CH$_3$ | S | syn |
| 139 | 3'-, F | CH$_3$ | S | syn |
| 140 | 3'-, Phenoxy | CH$_3$ | S | syn |

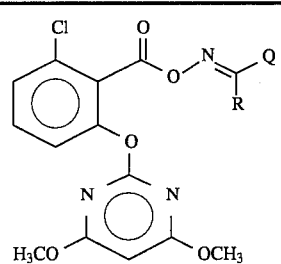 (I-d)

| Compound No. | Q | R | Isomerism (ratio) |
|---|---|---|---|

TABLE 1-continued

| Compound No. | Q | R | Isomerism |
|---|---|---|---|
| 141 | 4-pyridyl | H | |
| 142 | 2-furyl | H | |
| 143 | 3-furyl | H | |
| 144 | 5-nitro-2-furyl | H | |
| 145 | 5-methyl-2-furyl | H | |
| 146 | 2-thienyl | H | |
| 147 | 3-thienyl | H | |
| 148 | 5-methyl-2-thienyl | H | |
| 149 | 5-nitro-2-thienyl | H | |
| 150 | N-methyl-2-pyrrolyl | H | |
| 151 | 4-pyridyl | CH$_3$ | syn |
| 152 | 2-furyl | CH$_3$ | syn + anti (3:1) |
| 153 | 5-methyl-2-furyl | CH$_3$ | syn |
| 154 | 5-methyl-2-furyl | Cl | syn |
| 155 | 5-methyl-2-furyl | SCH$_3$ | syn |
| 156 | 5-methyl-2-furyl | OCH$_3$ | syn |

TABLE 1-continued

| No. | Structure | R | Isomer |
|---|---|---|---|
| 157 | 2,5-dimethyl-furan-3-yl | OCH₃ | anti |
| 158 | benzofuran-2-yl | CH₃ | syn |
| 159 | 2,5-dimethyl-furan-3-yl (with 4-CH₃) | CH₃ | syn |
| 160 | 5-methyl-furan-2-yl | COOCH₃ | syn + anti (1:3) |
| 161 | 5-methyl-thiophen-2-yl | CH₃ | syn |
| 162 | 5-methyl-thiophen-2-yl | CH₃ | anti |
| 163 | 4-methyl-thiophen-2-yl | CH₃ | syn |
| 164 | 5-methyl-thiophen-2-yl | COOCH₃ | anti |
| 165 | 4-methyl-thiophen-2-yl | COOCH₃ | syn + anti (1:3) |
| 166 | 5-chloro-thiophen-2-yl | CH₃ | syn |
| 167 | 5-chloro-thiophen-2-yl | CH₃ | anti |
| 168 | 3-H₃₃C-thiophen-2-yl | CH₃ | syn |
| 169 | 2,5-dimethyl-thiophen-3-yl | CH₃ | syn |
| 170 | 2,5-dimethyl-furan-3-yl (with 4-CH₃) | CH₃ | syn |
| 171 | 2-methyl-5-ethyl-thiophen-3-yl (4-CH₃) | SCH₃ | syn |
| 172 | N-methyl-pyrrol-2-yl | CH₃ | syn |
| 173 | N-methyl-pyrrol-3-yl | CH₃ | anti |
| 174 | CH₃ | CN | |
| 175 | C₂H₅ | CN | |
| 176 | phenyl | CN | |
| 177 | 2-methylphenyl | CN | |
| 178 | 3,5-dimethylphenyl | CN | |
| 179 | 2,4-dimethylphenyl | CN | |
| 180 | 4-methoxyphenyl | CN | |
| 181 | 4-ethoxyphenyl | CN | |
| 182 | 4-ethylphenyl | CN | |
| 183 | 4-chlorophenyl | CN | |
| 184 | 3-chlorophenyl | CN | |
| 185 | 4-fluorophenyl | CN | |

(I-e)

Structure: 2-chloro-6-[(4,6-dimethoxypyrimidin-2-yl)oxy]benzoic acid O-acyl oxime linked to a 2-oxo-2-(phenyl-Rᵃ)acetyl group, Q substituent on the oxime carbon.

TABLE 1-continued
| Compound No. | Q | Rᵃ |
|---|---|---|
| 186 | H | H |
| 187 | CH₃ | H |
| 188 | n-C₃H₇ | H |
| 189 | n-C₄H₉ | H |
| 190 | 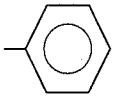 | H |
| 191 | H | 3-Br |
| 192 | CH₃ | 4-F |
| 193 | Cl | H |
| 194 | CH₃S | H |
| 195 | 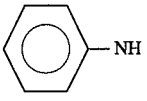 | H |
| 196 | 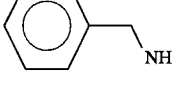 | H |
| 197 | 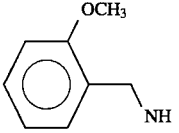 | H |
| 198 | 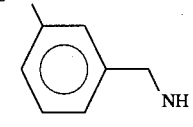 | H |
| 199 | 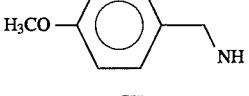 | H |
| 200 | 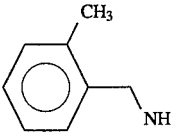 | H |
| 201 | 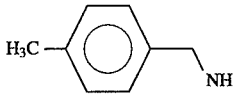 | H |
| 202 | 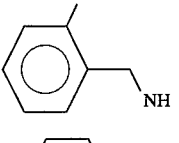 | H |
| 203 | 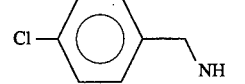 | H |
| 204 | 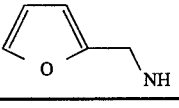 | H |
TABLE 1-continued
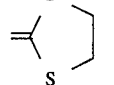
(I-f)
| Compound No. | Q | R³ | Z |
|---|---|---|---|
| 205 | n-C₃H₇ | CH₃ | S |
| 206 | n-C₄H₉ | CH₃ | S |
| 207 | CH₃ | C₂H₅ | O |
| 208 | CH₃S | CH₃ | S |
| 209 | 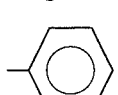 | | |
| 210 | n-C₃H₇ |  | NH |
| 211 | n-C₄H₉ | 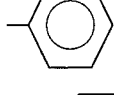 | NH |
| 212 | n-C₃H₇ | 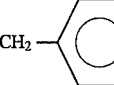 | NH |
| 213 | n-C₄H₉ | 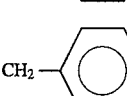 | NH |
| 214 | CH₃ |  | |
| 215 | n-C₃H₇ | 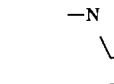 | |
| 216 | n-C₄H₉ | 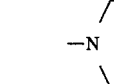 | |
| 217 | 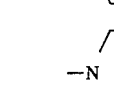 | | |
| 218 |  | | |

TABLE 1-continued

| 219 | 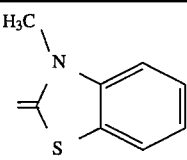 |
|---|---|

Generally, it has been known that 2-(pyrimidin-2-yl)oxybenzoic acid derivative needs to have a substituentes (especially, chlorine atom) on 6-position of its benzene moiety for more potential herbicidal activity. But, in this case, there are some difficulties in preparing imino ester derivatives of 2-(pyrimidin-2-yl)oxybenzoic acid, caused by its structural characteristics, and therefore, typically known 2-(pyrimidin-2-yl)oxybenzoic acid imino esters have no substituentes on 6-position of their benzene ring. For example, European Patent Publication No. 346,789 disclosed simple imino esters derived from oxime compounds which are synthesized by using acetone, cyclohexane or cyclopentane. There is, however, no description with respect to processes for the preparation thereof or herbicidal effects of the same.

In above publication, there is also disclosed only one compound of imino ester derived from acetophenone oxime similar to the compounds of this invention without any detailed description about its herbicial activities. Moreover, the imino ester compounds of the present invention cannot be produced by the methods described in the said publication, even though, in some particular cases, they can be synthesized only with extremely low yields (less than 5).

In such benzoic acid compounds having substituentes on their 2,6-positions as shown in the formula (I) of the present invention, the carboxyl groups of the compounds are seriously suffered with steric hindrance. For that reason, it is very difficult to produce those imino-oxy ester derivatives by using generally known preparing method with high yield [Reference: Tetrahedron, Vol. 36, p 2409 (1980) and J. Org. Chem., Vol. 35, p 1198 (1970)]. Furthermore, the reaction of esterification of steric hindered benzoic acid needs strongly acidic condition, so that the reaction under this condition is not adaptable to prepare the compounds according to the present invention.

In these circumstances, as main intermediate useful for preparing the compounds of formula (I) without said problems of above known methods, the present invention also provides a novel pyridine mercapto ester having the following formula (II):

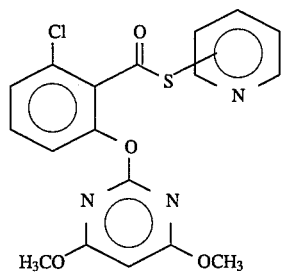

The above pyridine mercapto ester of formula (II) is very useful for preparing not only imino-oxy ester compounds according to the present invention, but also most of ester compounds hardly preparable with generally known methods in the art.

The compounds of formula (II) can be produced by reacting 6-chloro-2-(4,6-dimethoxypyrimidin-2-yl)oxybenzoic acid for formula (X) and 2,2'-dipyridylsulfide or 4,4'-dipyridylsulfide in the presence of trialkyl or triphenylphosphine and a solvent as illustrated in the following scheme (A). This process also constitutes a further aspect of the invention.

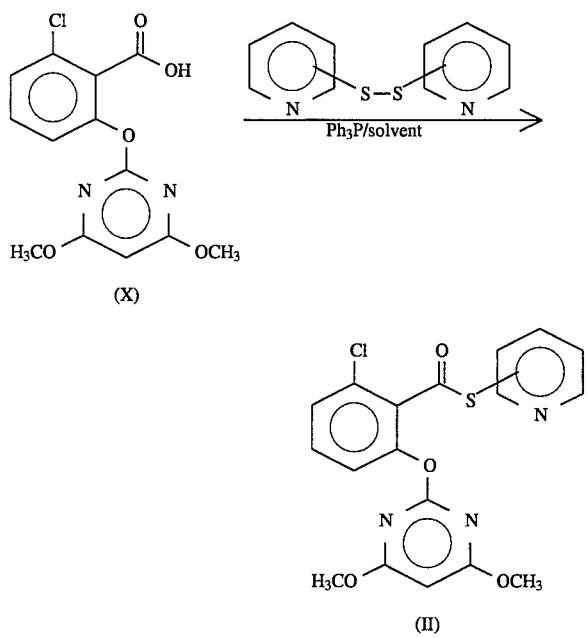

The starting material, the compound (X), employed in this process can be prepared in accordance with the methods disclosed in European Patent Publication No. 249,708.

Here, as the solvent, there may be employed acetone, benzene, toluene, ethyl acetate, methylene chloride, chloroform or 1,2-dichloroethane.

6-Chloro-2-(4,6-dimethoxypyrimidin-2-yl)oxybenzoic acid imino esters represented by formula (I) of the present invention can be prepared by reacting the compound of the following formula (II) and the compound of the following formula (III) in the presence of a solvent as illustrated in the following scheme (B). This process constitutes a still further aspect of the invention.

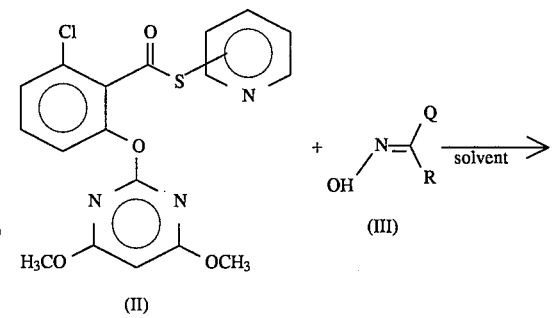

17
-continued
SCHEME (B)

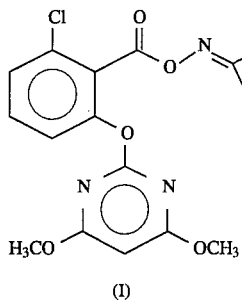

SCHEME (E)

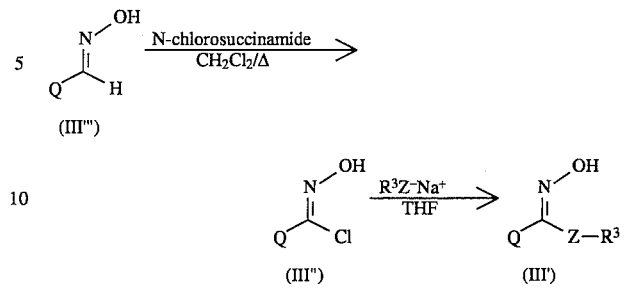

In the above formulas, R and Q are as defined above.

The reaction according to the scheme (B) can be carried out from room temperature to boiling point of the solvent.

When the reaction is conducted in room temperature, it is desirable to carry out the reaction in the presence of metal salt, preferably copper (II) salt such as $CuBr_2$, $CuCl_2$ and so on.

Here, as the solvent, there may be employed a halogenated hydrocarbon solvent such as methylene chloride, chloroform, tetrachloromethane or 1,2-dichloro ethane, a nitrilic solvent such as acetonitrile or propionitrile. But the solvent is not restricted to such examples.

Whereas, when the reaction is conducted in boiling point of the solvent, the reaction may be conducted without metal salt, but it is more preferable to carry out the reaction using a solvent having higher boing point such as xylene.

The compound of formula (III) can be easily prepared by using a generally disclosed procedure in the art. For example, it can be prepared by reacting the keto compound of formula (IV) and hydroxylamine along with the following schame (C):

SCHEME (C)

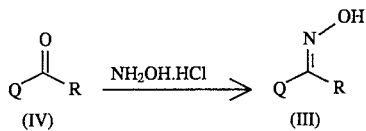

wherein,

R and Q are as defined above.

And, the compound of formula (III) can be also prepared by reacting the acyl compound of formula (V) and alkylnitrite in the acidic condition as illustrated in the following scheme (D):

SCHEME (D)

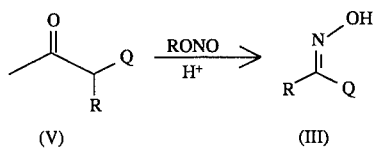

wherein,

R and Q are as defined above.

Further, among the compounds of formula (III), when R is $-Z-R^3$ and Z is oxygen or sulfur atom, or the compound of the following formula (III') can be prepared from the aldehyde oxime compound of formula (III''') widely known in the art, for example, as illustrated in the following scheme (E):

wherein, Q, and $R^3$ are as defined above, and Z is an oxygen or a sulfur atom.

Now, the present invention will be described in further detail with reference to Examples. However, it should be understood that the present invention is by no means restricted to such specific Examples.

PREPARATION 1

Preparation of 6-Chloro-2-[(4,6-dimethoxypyrimidin-2-yl)oxy]benzoic acid 2-pyridylthio ester (II-1)

31.0 g of 6-chloro-2-[(4,6-dimethoxypyrimidin-2-yl)oxy] benzoic acid, 22.0 g of 2,2'-dipyridylsulfide and 26.2 g of triphenylphosphine were suspended in 250 ml of toluene, and were violently stirred at room temperature for 3 hours. The reaction mixture was filtered, and the toluene was distilled off under reduced pressure. The residue thus obtained was purified by silica gel column chromatography to obtain 36.3 g of the above identified compound as a white crystal (yield 90%).

$^1$H NMR (CDCl$_3$, δ): 3.83(s, 6H), 5.79(s, 1H), 7,18(d, 1H), 7.3–7.4(m,3H), 7.74(d, 2H), 8.60(d, 1H).

PREPARATION 2

Preparation of 6-Chloro-2-[(4,6-dimethoxypyrimidin-2-yl)oxy]benzoic acid 4-pyridylthio ester (II-2)

31.0 g of 6-chloro-2-[(4,6-dimethoxypyrimidin-2-yl)oxy] benzoic acid, 22.0 g of 4,4'-dipyridylsulfide and 26.2 g of triphenylphosphine were suspended in 250 ml of toluene, and were violently stirred at room temperature for 2 hours. The reaction mixture was filtered, and the toluene was distilled off under reduced pressure. The residue thus obtained was purified by silica gel column chromatography to obtain 36.0 g of the above identified compound as a white crystal (yield 90%).

$^1$H NMR (CDCl$_3$, δ): 3.82(s, 6H), 5.78(s, 1H), 7.2–7.6(m, 5H), 8.64(d, 1H.

PREPARATION 3

Preparation of Benzaldehyde Oxime (III-1)

10.6 g of benzaldehyde, 7.0 g of hydroxylamine HCl salt and 14.0 g of potassium carbonate were suspended in 200 ml of methanol, and were stirred at room temperature for 5 hours. The reaction mixture was filtered, and the methanol was distilled off under reduced pressure. The residue thus obtained was purified by silica gel column chromatography to obtain 12.0 g of the above identified compound as a white crystal (yield 99%).

In the same manner as described in Preparation 3, a number of benzaldehyde oxime compounds (III) with various substituentes were prepared from benzaldehyde compounds (IV).

PREPARATION 4

Preparation of 3-Pyridylaldehyde Oxime (III-2)

11.3 g of 3-pyridyladehyde, 7.0 g of hydroxylamine HCl salt and 14.0 g of potassium carbonate were suspended in 200 ml of methanol, and were stirred at room temperature for 5 hours. The reaction mixture was filtered, and the methanol was distilled off under reduced pressure. The residue thus obtained was purified by silica gel column chromatography to obtain 11.3 g of the above identified compound as a white crystal (yield 88%).

PREPARATION 5

Preparation of 2-Furylzaldehyde Oxime (III-2)

9.6 g of 2-furylaldehyde, 7.0 g of hydroxylamine HCl salt and 14.0 g of potassium carbonate were suspended in 200 ml of methanol, and were stirred at room temperature for 5 hours. The reaction mixture was filtered, and the methanol was distilled off under reduced pressure. The residue thus obtained was purified by silica gel column chromatography to obtain 11.0 g of the above identified compound as a white crystal (yield 98%).

PREPARATION 6

Preparation of Oxime(Q=2-methyl-5-furyl, R=CH$_3$: III-3)

12.4 g of 2-acetyl-5-methylfurane, 7.0 g of hydroxylamine HCl salt and 14.0 g of potassium carbonate were suspended in 200 ml of methanol, and were stirred at room temperature for 5 hours. The reaction mixture was filtered, and the methanol was distilled off under reduced pressure. The residue thus obtained was purified by silica gel column chromatography to obtain 14.0 g of the above identified compound as a white crystal (yield 99).

In the same manner as described in Preparation 4 or 5, a number of heteroaryl aldehyde oxime compounds (III) with various substituentes, such as (III-4: Q=3-pyridyl, R=CH$_3$), (III-5: Q=2-furyl, R=CH$_3$), (III-6: Q=2-benzofuryl, R=CH$_3$), III-7: Q=2,5-dimethyl-3-furyl, R=CH$_3$), (III-8: Q=2-furyl, R=COOCH$_3$), III-9: Q=2-thienyl, R=CH$_3$), III-10: Q=3-thienyl, R=CH$_3$), (III-11: Q=2-thienyl, R=COOCH$_3$), (III-12: Q=3-thienyl, R=COOCH$_3$), (III-13: Q=2-chloro-5-thienyl, R=CH$_3$), (III-14: Q=3-methyl-2-thienyl, R=CH$_3$), (III-15: Q=2-methyl-5-thienyl, R=CH$_3$), III-16: Q=2,5-dimethyl-3-thienyl, R=CH$_3$) and (III-17: Q=N-methyl-3-pyrrolyl, R=CH$_3$), were prepared from heteroarylaldehyde or ketone compounds (IV).

PREPARATION 7

Preparation of Oxime (III-18: Q=2-methyl-5-furyl, R=Cl)

12.5 g of 2-methyl-5-furylaldehyde oxime and 13.4 g of N-chlorosuccinimide were suspended in 200 ml of methylene chloride, and were stirred under reflux of methylene chloride for 3 hours. The reaction mixture was filtered, and the methylene chloride was distilled off under reduced pressure. The residue thus obtained was purified by silica gel column chromatography to obtain 11.2 g of the above identified compound (yield 80%).

PREPARATION 8

Preparation of Oxime (III-19: Q=2-methyl-5-furyl, R=SCH$_3$)

14.0 g of oxime compound (III-18) prepared in Preparation 6 was dissolved in 100 ml of tetrahydrofurane and 7.1 g of sodium thiomethoxide was slowly added to the solution for 5 minutes while stirring. After 1 hour, 100 ml of saturated ammonium chloride solution was added, and extracted with 200 ml of ethyl acetate. The extract was dried over anhydrous magnesium sulfate, and then the solvent was distilled off under reduced pressure. The residue thus obtained was purified by silica gel column chromatography to obtain 14.0 g of the above identified compound (yield 95%).

PREPARATION 9

Preparation of Oxime (III-20: Q=phenyl, R=CN)

10.6 g of benzoylcyanide (IV-3), 7.0 g of hydroxylamine HCl salt and 14.0 g of potassium carbonate were suspended in 200 ml of methanol, and were stirred at room temperature for 5 hours. The reaction mixture was filtered, and the methanol was distilled off under reduced pressure. The residue thus obtained was purified by silica gel column chromatography to obtain 14.2 g of the above identified compound as a white crystal (yield 99%).

In the same manner as described in Preparation 8, a number of benzoyl cyanide oxime compounds (III) with various substituentes were easily prepared from nitrile compounds (IV).

PREPARATION 10

Preparation of Oxime (III-21: Q=p-methoxyphenyl, R=CN)

14.7 g of p-methoxybenzoylcyanide (IV-3) and 12.0 g of potassium t-butoxide were added to 100 ml of t-butanol, and were stirred at room temperature for 5 hours. After the reaction mixture was cooled down to 0° C., 11.0 g of butylnitride was slowly added to the mixture and stirred for 30 minutes. 100 ml of saturated ammonium chloride solution was added, and extracted with 200 ml of ethyl acetate. The extract was dried over anhydrous magnesium sulfate, and then the solvent was distilled off under reduced pressure. The residue thus obtained was purified by silica gel column chromatography to obtain 12.1 g of the above identified compound (yield 80%).

PREPARATION 11

Preparation of Compound (III"-1: Q=phenyl)

12.1 g of benzaldehyde oxime and 14.0 g of N-chlorosuccinimide were added in 200 ml of methylene chloride, and were stirred under reflux of methylene chloride for 2 hours. The reaction mixture was filtered, and the methylene chloride was distilled off under reduced pressure. The residue thus obtained was purified by silica gel column chromatography to obtain 15.0 g of the above identified compound (yield 98%).

In the same manner as described in Preparation 10, a number of compounds (III") with various substituentes, such as (III"-4: Q=2-methyl phenyl), (III"05: Q=3-methylphenyl), (III"-6: Q=4-methylphenyl), (III"-7: Q=4-ethylphenyl), (III"-8: Q=4-methoxyphenyl), (III"-9: Q=3-chlorophenyl), (III"-10: Q=4-chlorophenyl), (III"-11: Q=4-fluorophenyl), (III"-14: Q=4--methyl thiophenyl), (III"-15: Q=4-cyanophenyl), (III"-16: Q=4-trichloro methylphenyl), (III"-17: Q=4-(N,N-dimethyl)phenyl), (III"-25: Q=4-propyl phenyl), (III"-33: Q=3-fluorophenyl) and (III"-34: Q=4-phenoxy phenyl) were prepared from benzaldehyde oxime compounds (III''').

PREPARATION 12

Preparation of Oxime (III'-1: Q=phenyl, R=OCH$_3$)

15.6 g of oxime compound (III"-1) prepared in Preparation 10 was dissolved in 100 ml of tetrahydrofurane and 6.0 g of sodium methoxide was slowly added in the solution, and stirred at room temperature for 5 hours. The reaction mixture was filtered, and the solvent was distilled off under reduced pressure. The residue thus obtained was purified by silica gel column chromatography to obtain 7.5 g of the above identified compound (yield 50%).

In the same manner as described in Preparation 10, a number of compounds (III') with various substituentes, such as (III'-4: Q=2-methyl phenyl, R=OCH$_3$), (III'-5: Q=3-methyl phenyl, R=OCH$_3$), (III'-6: Q=4-methyl phenyl, R=OCH$_3$), (III'-7: Q=4-ethylphenyl, R=OCH$_3$), (III'-8: Q=4-methoxy phenyl, R=OCH$_3$), (III'-9: Q=3-chlorophenyl, R=OCH$_3$), (III'-10: Q=4-chloro phenyl, R=OCH$_3$), (III'-11: Q=4-fluorophenyl, R=OCH$_3$), (III'-14: Q=4-methyl thiophenyl, R=OCH$_3$), (III'-15: Q=4-cyanophenyl, R=OCH$_3$), (III'-16: Q=4-tri chloromethylphenyl, R=OCH$_3$), (III'-17: Q=4-N,N-dimethyl)phenyl, R=OCH$_3$), were prepared from oxime compounds (III").

PREPARATION 13

Preparation of Oxime (III'-18: Q=phenyl, R=SCH$_3$)

15.6 g of oxime compound (III"-1) prepared in Preparation 10 and 15.6 g of sodium thiomethoxide was added in 100 ml of tetrahydrofurane and stirred at room temperature for 1 hours. The reaction mixture was filtered, and the solvent was distilled off under reduced pressure. The residue thus obtained was purified by silica gel column chromatography to obtain 18.0 g of the above identified compound (yield 90%).

In the same manner as described in Preparation 12, a number of compounds (III') with various substituentes, such as from (III'-19: Q=phenyl, R=SCH$_2$CH$_3$) to (III'-34: Q=4-phenoxyphenyl, R=SCH$_3$), were prepared from oxime compounds (III").

EXAMPLE 1

Synthesis of Compound No. 1 (Q=CH$_3$, R=OCH$_3$)

183 mg of thioester compound (II-1) prepared in Preparation 1 and 75 mg of 2-hydroxyiminopropoinic acid methyl ester were dissolved in 10 ml of xylene and were stirred under reflux of xylene for 30 minutes. the xylene was distilled off under reduced pressure. The residue thus obtained was purified by silica gel column chromatography to obtain 43 mg of the above identified compound (yield 23%).

$^1$H NMR (CDCl$_3$, δ): 2.15(s, 3H), 3.80(s, 6H), 3.98(s, 3H), 5.77(s, 1H), 7.20(d, 1H), 7.35(d, 1H), 7.45(t, 1H).

EXAMPLE 2

Synthesis of Compound No. 2 (Q=CH$_3$, R=OCH$_2$CH$_3$)

848 mg of thioester compound (II-1) prepared in Preparation 1 and 236 mg of 2-hydroxyiminopropoinic acid ethyl ester were dissolved in 5 ml of methylene chloride, and 470 mg of CuBr$_2$ was added in the reaction mixture as stirred at room temperature. After stir for another 1 hour, the solvent was distilled off under reduced pressure. The residue thus obtained was purified by silica gel column chromatography to obtain 486 mg of the above identified compound (yield 64%).

$^1$H NMR (CDCl$_3$, δ): 1.36(t, 3H), 2.14(s, 3H), 3.80(s, 6H), 4.35(q, 2H), 5.77(s, 1H), 7.20(d, 1H), 7.35(d, 1H), 7.45(t, 1H); Mass(FAB): 424(M+1), 293.

In the similar manner as described in Example 1 or 2, the compound No. 3–28 were prepared by reacting a thioester (II-1) or (II-2) and a corresponding hydroxyimino compound, and the physical properties thereof are given below in Table (2-1)

TABLE (2-1)

| Compd. No. | $^1$H NMR(CDCl$_3$) δ ppm | Mass (FAB) |
|---|---|---|
| 3 | 0.96(t, 3H), 1.75(m, 2H), 2.14(s, 3H), 3.81(s, 6H), 4.22(q, 2H), 5.77(s, 1H), 7.35(d, 1H), 7.42(t, 1H) | 438 (M + 1) |
| 4 | 1.34(d, 6H), 2.01(s, 3H), 3.81(s, 6H), 5.16(m, 1H), 5.77(s, 2H), 7.21(d, 1H), 7.36(d, 1H), 7.43(t, 1H) | 438 (M + 1) |
| 5 | 2.12(s, 3H), 3.81(s, 6H), 4.75(d, 2H), 5.32(m, 2H), 5.77(s, 1H), 5.95(m, 1H), 7.21(d, 1H), 7.35(d, 1H), 7.43(s, 1H) | 436 (M + 1) |
| 6 | 0.94(t, 3H), 1.39(m, 2H), 1.71(t, 2H), 2.14(s, 3H), 3.81(s, 6H), 5.77(s, 1H), 7.21(d, 1H), 7.35(d, 1H), 7.43(t, 1H) | 452 (M + 1) |
| 7 | 0.87(t, 3H), 1.28(m, 10H), 1.72(t, 2H), 2.11(s, 3H), 3.81(s, 6H), 4.25(t, 2H), 5.77(s, 1H), 7.21(d, 1H), 7.35(d, 1H), 7.43(t, 1H) | 508 (M + 1) |
| 8 | 2.11(s, 3H), 3.80(s, 6H). 5.32(s, 2H), 5.77(s, 6H), 7.21(d, 2H), 7.36(m, 7H) | 486 (M + 1) |
| 9 | 1.07(t, 3H), 1.36(t, 3H), 2.61(q, 2H), 3.80(s, 6H), 4.34(q, 2H), 5.77(s, 1H), 7.20(d, 1H), 7.34(d, 1H), 7.44(t, 1H) | 438 (M + 1) |
| 10 | 0.91(t, 3H), 1.57(m, 2H), 2.59(t, 2H), 3.79(s, 6H), 3.88(s, 3H), 5.77(s, 1H), 7.21(d, 1H), 7.36(d, 1H), 7.45(t, 1H) | 438 (M + 1) |
| 11 | 0.89(t, 3H), 1.36(t, 3H), 1.52(m, 2H), 2.59(t, 2H), 3.81(s, 6H), 4.36(q, 2H), 5.77(s, 1H), 7.21(d, 1H), 7.35(d, 1H) 7.43(t, 1H) | 452 (M + 1) |
| 12 | 1.16(d, 6H), 3.30(m, 1H), 3.81(s, 6H), 3.87(s, 3H), 5.77(s, 1H), 7.20(d, 1H), 7.34(d, 1H), 7.45(t, 1H) | 438 (M + 1) |
| 13 | 1.13(d, 6H), 1.34(t, 3H), 3.31(m, 1H), 3.81(s, 6H), 4.28(q, 2H), 5.77(s, 1H), 7.21(d, 1H), 7.35(d, 1H), 7.43(t, 1H) | 452 (M + 1) |
| 14 | 1.36(t, 3H), 3,37(d, 2H), 3.81(s, 6H), 4.33(q, 2H), 5.08(m, 2H), 5.70(m, 1H), 5.77(s, 1H), 7.21(d, 1H), 7.35(d, 1H), 7.43(t, 1H) | 493 (M + 1) |
| 15 | 0.85(t, 3H), 1.28(m, 2H), 1.47(m, 2H), 2.62(t, 2H), 3.81(s, 6H), 3.90(s, 3H), 5.77(s, 1H), 7.21(d, 1H), 7.35(d, 1H) 7.43(t, 1H) | 452 (M + 1) |
| 16 | 0.88(t, 3H), 1.29(m, 2H), 1.39(t, 2H), 1.48(m, 2H), 2.62(t, 2H), 3.81(s, 6H), 4.35(q, 2H), 5.77(s, 1H), 7.21(d, 1H) 7.34(d, 1H), 7.43(t, 1H) | 466 (M + 1) |
| 17 | 0.87(t, 3H), 0.93(t, 3H), 1.30(m, 2H), 1.30(m, 2H), 1.46(m, 2H), 1.76(m, 2H), 2.59(t, 2H) 3.82(s, 6H), | 480 (M + 1) |

TABLE (2-1)-continued

| Compd. No. | $^1$H NMR(CDCl$_3$) δ ppm | Mass (FAB) |
|---|---|---|
|  | 4.23(t, 2H), 5.77(s, 1H), 7.21(d, 1H), 7.35(d, 1H), 7.43(t, 1H) |  |
| 18 | 0.86(d, 6H), 1.97(m12H), 2.52(d, 2H), 3.81(s, 6H), 3.85(s, 3H), 5.77(s, 1H), 7.21(d, 1H), 7.34(d, 1H), 7.43(t, 1H) | 452 (M + 1) |
| 19 | 0.87(t, 3H), 0.98(d, 1H), 2.16(m, 1H), 2.63(d, 2H), 3.81(s, 6H), 4.20(q, 2H), 5.77(s, 1H) 7.21(d, 1H), 7.35(d, 1H), 7.43(t, 1H) | 466 (M + 1) |
| 20 | 1.25(t, 3H), 3.84(s, 6H), 3.99(s, 2H), 4.24(q, 2H), 5.76(s, 1H), 7.22(m, 6H) 7.36(d, 1H), 7.43(t, 1H) | 500 (M + 1) |
| 21 | 0.86(d, 6H), 1.36(t, 3H), 1.50(m, 2H), 1.60(m, 2H), 2.59(t, 2H), 3.83(s, 6H), 4.35(q, 2H), 5.77(s, 1H), 7.20(d, 1H), | 480 (M + 1) |
| 22 | 1.16~1.75(m, 13H), 3.04(m, 1H), 3.82(s, 6H), 4.32(q, 2H), 5.77(s, 1H), 7.22(d, 1H), 7.35(d, 1H), 7.43(t, 1H) | 492 (M + 1) |
| 23 | 0.85(t, 3H), 1.18~1.55(m, 6H), 2.59(t, 2H), 3.81(s, 6H), 4.32(t, 2H), 5.77(s, 1H), 7.21(d, 1H), 7.34(d, 1H), 7.43(t, 1H) | 480 (M + 1) |
| 24 | 0.85(t, 3H), 1.15~1.52(m, 12H), 2.59(t, 2H), 3.81(s, 6H), 4.32(t, 2H), 5.77(s, 1H), 7.21(d, 1H), 7.34(d, 1H), 7.43(t, 1H) | 522 (M + 1) |
| 25 | 0.86(s, 3H), 1.11(d, 3H), 1.35(t, 3H), 1.48(m, 1H), 1.63(m, 1H), 3.13(s, 1H), 3.81(s, 6H), 4.29(q, 2H), 5.77(s, 1H), 7.21(d, 1H), 7.34(d, 1H), 7.43(t, 1H) | 466 (M + 1) |
| 26 | 0.85(t, 3H), 1.34(t, 3H), 1.71(m, 1H), 1.92(m, 1H), 2.02(s, 3H), 3.80(s, 6H), 4.35(m, 2H), 5.77(s, 1H), 7.21(d, 1H), 7.34(d, 1H), 7.43(t, 1H) | 512 (M + 1) |
| 27 | 1.10(t, 3H), 1.36(t, 3H), 2.95(t, 2H), 3.40(q, 2H), 3.58(t, 2H), 3.80(s, 6H), 4.36(q, 2H), 5.77(s, 1H), 7.20(d, 1H), 7.34(d, 1H), 7.423(t, 1H) | 482 (M + 1) |
| 28 | 2.10(s, 3H), 2.48(s, 3H), 3.82(s, 6H), 5.77(s, 1H), 7.22(d, 1H), 7.38(d, 1H), 7.47(t, 1H) | 394 (M + 1) |

EXAMPLE 3

Synthesis of Compound No. 29a (Q=phenyl, R=COOCH$_3$)

404 mg of thioester compound (II-1) prepared in Preparation 1 and 195 mg of 2-hydroxyimino-2-phenylacetic acid methyl ester were dissolved in 5 ml of methylene chloride, and 250 mg of CuBr$_2$ was added in the reaction mixture as stirred at room temperature. After stir for another 1 hour, the solvent was distilled off under reduced pressure. The residue thus obtained was purified by silica gel column chromatography to obtain 328 mg of the above identified compound (yield 69%).

$^1$H NMR (CDCl$_3$, δ): 3.81(s, 6H), 3.91(s, 3H), 5.78(s, 1H), 7.21(d, 1H), 7.3–7.5(m, 5H), 7.67(d, 2H); Mass(FAB): 472(M+1), 293.

In the similar manner as described in Example 29a, the compound No. 29b–56b were prepared by reacting a thioester (II-1) or (II-2) and a corresponding hydroxyimino compound, and the physical properties thereof are given below in Table (2-2)

TABLE (2-2)

| Compd. No. | $^1$H NMR(CDCl$_3$) δ ppm | Mass (FAB) |
|---|---|---|
| 29b | 3.74(s, 6H), 3.93(s, 3H), 5.73(s, 1H), 7.14(d, 1H), 7.26–7.70(m, 7H) | 472 (M + 1) |
| 30 | 1.31(t, 3H), 3.30(s, 6H), 4.40(q, 2H), 5.77(s, 1H), 7.19–7.70(m, 8H) | 486 (M + 1) |
| 31a | 0.89(t, 3H), 1.70(m, 2H), 3.83(s, 6H), 4.29(t, 2H), 5.77(s, 1H), 7.12–7.70(m, 8H) | 500 (M + 1) |
| 31b | 0.96(t, 3H), 1.76(m, 2H), 3.75(s, 6H), 4.29(t, 2H), 5.74(s, 1H), 7.12–7.70(m, 8H) | 500 (M + 1) |
| 32 | 1.29(d, 6H), 3.82(s, 6H), 5.24(m, 1H), 5.77(s, 1H), 7.15–7.72(m, 8H) | 500 (M + 1) |
| 33 | 3.81(s, 6H), 4.82(d, 2H), 5.18–5.46(m, 2H) 5.77(s, 1H), 5.94(m, 1H), 6.96–7.78(m, 8H) | 498 (M + 1) |
| 34 | 3.80(s, 6H), 5.45(s, 2H), 5.77(s, 1H), 7.21–7.78(m, 13H) | 548 (M + 1) |
| 35 | 3.81(s, 6H), 5.32(s, 2H), 5.77(s, 1H), 6.29(m, 1H), 6.43(d, 1H), 7.21–7.64(m, 9H) | 538 (M + 1) |
| 36 | 3.80(s, 6H), 5.45(s, 2H), 5.77(s, 1H), 6.98–7.68(m, 11H) | 554 (M + 1) |
| 37 | 1.25–1.54(m, 6H), 3.30–3.60(m, 2H), 3.82(s, 6H), 3.94(m, 1H), 4.20(m, 2H), 5.77(s, 1H), 7.18–7.74(m, 8H) | 556 (M + 1) |
| 38 | 3.80(s, 6H), 3.91(s, 3H), 5.76(s, 1H), 7.15–7.70(m, 7H) | 506 (M + 1) |
| 39 | 3.82(s, 6H), 3.91(s, 3H), 5.76(s, 1H), 7.20–7.70(m, 7H) | 506 (M + 1) |
| 40 | 1.30(t, 3H), 3.81(s, 6H), 4.39(q, 2H), 5.78(s, 1H), 7.2–7.8(m, 7H) | 520 (M + 1) |
| 41 | 3.81(s, 6H), 3.91(s, 3H), 5.76(s, 1H), 7.08–7.77(m, 7H) | 490 (M + 1) |
| 42 | 3.82(s, 6H), 3.94(s, 3H), 5.79(s, 1H), 7.22(d, 1H), 7.3–7.8(m, 11H) | 548 (M + 1) |
| 43a | 1.29–1.41(t+t, 6H), 2.37(s, 3H), 3.82(s, 6H), 4.39(q, 2H), 5.77(s, 1H), 7.22–7.58(m, 7H) | 556 (M + 1) |
| 43b | 1.39(t, 3H), 2.35(s, 6H), 3.77(s, 6H), 4.39(q, 2H), 5.72(s, 1H), 7.22–7.42(m, 7H) | 500 (M + 1) |
| 44 | 2.43(s, 3H), 3.81(s, 6H), 3.85(s, 3H), 5.77(s, 1H), 7.21(d, 1H), 7.30(m, 4H), 7.35(d, 1H), 7.43(t, 1H) | 486 (M + 1) |
| 45 | 2.38(s, 3H), 3.85(s, 6H), 3.92(s, 3H), 5.77(s, 1H), 7.18–7.44(m, 14H) | 486 (M + 1) |
| 46a | 2.28(s+s, 6H), 3.81(s, 6H), 3.90(s, 3H), 5.77(s, 1H), 7.18–7.49(m, 14H) | 500 (M + 1) |
| 46b | 2.25(s+s, 6H), 3.81(s, 6H), 3.92(s, 3H), 5.74(s, 1H), 7.09–7.42(m, 6H) | 500 (M + 1) |
| 47 | 1.23(t, 3H), 2.68(q, 2H), 3.82(s, 6H), 3.90(s, 3H), 7.22(d, 2H), 7.36(d, 1H), 7.43(t, 1H), 7.60(m, 3H) | 500 (M + 1) |
| 48a | 3.74(s, 3H), 3.81(s, 3H), 3.94(s, 1.5H), 3.96(s, 1.5H), 5.74(s, 0.5H), 5.79(s, 0.5H), 7.16–7.95(m, 7H) | 540 (M + 1) |
| 48b | 3.74(s, 6H), 3.96(s, 3H), 5.74(s, 1H), 7.18(d, 1H), 7.31(d, 1H), 7.40(t, 1H), 7.51(t, 1H), 7.70(t, 2H), 7.85(s, 1H) | 540 (M + 1) |
| 49a | 3.79(s, 6H), 3.83(s, 3H), 3.90(s, 3H), 5.78(s, 1H), 7.30–7.44(m, 7H) | 502 (M + 1) |
| 49b | 3.74(s, 6H), 3.81(s, 3H), 3.92(s, 3H), 5.72(s, 1H), 6.92–7.44(m, 7H) | 502 (M + 1) |
| 50 | 3.83(s, 6H), 3.88(s, 3H), 3.92(s, 3H), 5.77(s, 1H), 6.82–7.65(m, 7H) | 502 (M + 1) |
| 51 | 1.33(t, 3H), 3.79(s, 6H), 3.83(s, 3H), 4.02(q, 2H), 5.77(s, 1H), 6.88(d, 1H), 6.96(t, 1H), 7.20(d, 1H), 7.33(d, 1H), 7.40(m, 2H), 7.83(d, 1H) | 516 (M + 1) |

TABLE (2-2)-continued

| Compd. No. | $^1$H NMR(CDCl$_3$) δ ppm | Mass (FAB) |
|---|---|---|
| 52 | 1.20(t, 3H), 3.72(s, 6H), 3.88(s, 3H), 4.10(q, 2H), 5.73(s, 1H), 7.10–7.70(m, 7H) | 516 (M + 1) |
| 53 | 1.40(t, 3H), 3.76(s, 6H), 3.90(s, 3H), 4.10(q, 2H), 5.73(s, 1H), 6.82(d, 2H), 7.12–7.50(m, 5H) | 516 (M + 1) |
| 54 | 2.94(s, 6H), 3.73(s, 6H), 3.92(s, 3H), 5.72(s, 1H), 6.78–7.42(m, 7H) | 515 (M + 1) |
| 55a | 3.39(s, 3H), 3.81(s, 6H), 3.91(s, 3H), 4.46(s, 2H), 5.77(s, 1H), 7.18–7.56(m, 7H) | 516 (M + 1) |
| 55b | 3.34(s, 3H), 3.75(s, 6H), 3.92(s, 3H), 4.46(s, 2H), 5.72(s, 1H), 7.18–7.56(m, 7H) | 516 (M + 1) |
| 56a | 1.65(s, 3H), 3.75(m, 2H), 3.82(s, 6H), 3.93(s, 3H), 4.05(m, 2H), 5.80(s, 1H), 7.20–7.89(m, 7H) | 558 (M + 1) |
| 56b | 1.62(s, 3H), 3.66(m, 2H), 3.76(s, 6H), 3.95(s, 3H), 3.96(m, 2H), 5.75(s, 1H), 7.18–7.68(m, 7H) | 558 (M + 1) |

EXAMPLE 4

Synthesis of Compound No. 57a (Q=3-acetylphenyl, R=COOCH$_3$)

252 mg of compound No. 56a, 25 ml of tetrahydrofurane, 25 ml of methanol, 13 ml of water and 2 ml of conc. HCl were mixed together and were stirred at room temperature for 20 hours. The solvent was distilled off under reduced pressure, and then extracted with ethyl acetate. The separated organic layer was dried over anhydrous magnesium sulfate and filtered. The solvent was distilled off under reduced pressure to obtain quantitatively the above identified compound $^1$H NMR (CDCS, δ): 2.63(s, 3H), 3.82(s, 6H), 3.94(s, 3H), 5.79(s, 1H), 7.26–8.21(m, 7H); Mass(FAB): 514(M+1), 293.

In the same manner as described in Example 4, the compound No. 57b was obtained quantitatively.

$^1$H NMR (CDCS, δ): 2.62(s, 3H), 3.74(s, 6H), 3.96(s, 2H), 5.73(s, 1H), 7.14–8.10(m, 7H); Mass(FAB): 5.14(M+1), 293.

EXAMPLE 5

Synthesis of Compound No. 58 (Q=CH$_3$, R=1-methoxycarbonyl-2-phenylethylamino)

404 mg of thioester compound (II-1) prepared in Preparation 1 and 282 mg of 2-hydroxyiminopropanoic acid (2-amino-3-phenylpropionic acid methyl ester)amide were dissolved in 7 ml of methylene chloride, and 265 mg of CuBr$_2$ was added in the reaction mixture as stirred at room temperature. After stir for another 1 hour, the solvent was distilled off under reduced pressure. The residue thus obtained was purified by silica gel column chromatography to obtain 412 mg of the above identified compound (yield 74%).

$^1$NMR (CDCl$_3$, δ): 2.05(s, 3H), 3.13(m, 2H), 3.70(s, 3H), 3.72(d, 1H), 3.18(s, 6H), 4.86(m, 1H), 5.79(s, 1H), 7.1–7.5(m, 8H); Mass(FAB): 557 (m+1), 293, 154.

In the similar manner as described in Example 5, the compound No. 59–63 were prepared, and the physical properties thereof are given below in Table (2-3)

TABLE (2-3)

| Compd. No. | $^1$H NMR(CDCl$_3$) δ ppm | Mass (FAB) |
|---|---|---|
| 59 | 2.98(s,3H), 3.07(s,3H), 3.79(s,6H), 5.78(s,1H), 7.21(d,1H), 7.40–7.50(m,5H), 7.74(d,2H) | 485 (M + 1) |
| 60 | 1.29(s,3H), 3.71(s,6H), 4.22(q,2H), 4.32(d,2H), 5.75(s,1H), 7.20(d,1H), 7.30–7.50(m,6H), 7.85(d,1H), 8.25(t,1H) | 543 (M + 1) |
| 61 | 1.24(t,6H), 3.74(s,6H), 4.25(q,2H), 5.74(s,1H), 7.20–7.80(m,8H) | 615 (M + 1) |
| 62a | 2.95–3.25(m,2H), 3.74(s,3H), 3.77(s,6H), 3.80(s,3H), 4.92–5.02(m,1H), 5.77(s,1H), 7.18(d,1H), 7.30–7.80(m,6H), 7.90(d,1H) | 601 (M + 1) |
| 62b | 2.90–3.20(m,2H), 3.62(s,3H), 3.69(s,3H), 3.72(s,6H), 5.13(m,1H), 5.74(s,1H), 7.21(d,1H), 7.30–7.60(m,5H), 7.80(d,2H), 8.32(d,1H) | 601 (M + 1) |
| 63 | 1.03(d,3H), 1.19(d+d,3H), 1.72(s+s,3H), 2.77(m,1H), 3.67(s,6H), 5.74(s,1H), 7.20–7.73(m,8H), 8.45(s,1H) | 558 (M + 1) |

EXAMPLE 6

Synthesis of Compound No. 64 (Q=phenyl, R=H)

4.0 g of thioester compound (II-1) prepared in Preparation 1 and 1.2 g of benzaldehyde oxime (III-1) were dissolved in 100 ml of xylene, and stirred for 30 minutes under reflux of xylene. The solvent was distilled off under reduced pressure. The residue thus obtained has purified by silica gel column chromatography to obtain 0.8 g of the above identified compound (yield 20%).

$^1$H NMR (CDCl$_3$, δ): 3.80(s, 6H), 5.77(s, 1H), 7.15–7.50(m, 6H), 7.70(d, 2H), 8.28(s, 1H); Mass(FAB): 414(M+1).

EXAMPLE 7

Synthesis of Compound No. 64 (Q=phenyl, R=H)

4.0 g of thioester compound (II-1) prepared in Preparation 1 and 1.2 g of benzaldehyde oxime (III-1) were dissolved in 50 ml of methylene chloride, and 2.2 g of CuBr$_2$ was added in the reaction mixture as stirred at room temperature. After stir for another 1 hour, the mixture was filtered and then the solvent was distilled off under reduced pressure. The residue thus obtained was purified by silica gel column chromatography to obtain 3.7 g of the above identified compound (yield 90%).

EXAMPLE 8

Synthesis of Compound No. 64 (Q=phenyl, R=H)

4.0 g of thioester compound (II-1) prepared in Preparation 2 and 1.2 g of benzaldehyde oxime (III-1) were dissolved in 50 ml of methylene chloride, and after 5 minutes, 2.2 g of CuBr$_2$ was added in the reaction mixture as stirred at room temperature. After stir for another 1 hour, the mixture was filtered and then the solvent was distilled off under reduced pressure. The residue thus obtained was purified by silica gel column chromatography to obtain 3.4 g of the above identified compound (yield 85%).

In the same manner as described in Example 7 or 8, the compound No. 65–106 were prepared, and the physical properties thereof are given below in Table (2-4)

TABLE (2-4)

| Compd. No. | $^1$H NMR(CDCl$_3$) δ ppm | Mass (FAB) |
|---|---|---|
| 65 | 2.38(s,3H), 3.79(s,6H), 5.77(s,1H), 7.15~7.50(m,6H), 7.80(d,1H), 8.52(s,1H) | 428 (M + 1) |
| 66 | 2.36(s,3H), 3.80(s,6H), 5.77(s,1H) 7.15~7.50(m,6H), 7.59(s,1H), 8.25(s,1H) | 428 (M + 1) |
| 67 | 2.38(s,3H), 3.79(s,6H), 5.76(s,1H) 7.15~7.50(m,5H), 7.59(d,2H), 8.23(s,1H) | 428 (M + 1) |
| 68 | 1.25(t,3H), 2.69(q,2H), 3.80(s,6H), 5.77(s,1H) 7.23~7.27(m,3H), 7.37~7.44(m,2H), 7.61(d,2H) 8.25(s,1H) | 442 (M + 1) |
| 69 | 1.26(d,6H), 2.93(m,1H), 3.80(s,6H), 7.21~7.45(m,5H), 7.62(d,2H), 8.25(s,1H) | 456 (M + 1) |
| 70 | 3.78(s,6H), 5.76(s,1H), 7.15~7.50(m,5H), 7.62(d,2H), 8.25(s,1H) | 448 (M + 1) |
| 71 | 3.80(s,6H), 5.78(s,1H), 7.21(d,1H) 7.33~7.58(m,5H), 7.74(s,1H), 8.25(s,1H) | 448 (M + 1) |
| 72 | 3.80(s,1H), 5.77(s,1H), 7.08~7.27(m,3H) 7.35~7.49(m,3H), 8.0(t,1H), 8.56(s,1H) | 432 (M + 1) |
| 73 | 3.76(s,6H), 5.77(s,1H), 7.12~7.22(m,3H) 7.34~7.39(d,1H), 7.42~7.50(m,3H), 8.26(s,1H) | 432 (M + 1) |
| 74 | 3.78(s,6H), 5.76(s,1H), 7.05~7.13(m,2H) 7.15~7.50(m,3H), 7.65~7.73(m,2H), 8.25(s,1H) | 432 (M + 1) |
| 75 | 3.79(s,6H), 3.85(s,3H), 5.77(s,1H), 6.91(d,2H) 7.15~7.50(m,3H), 7.64(d,2H), 8.21(s,1H) | 444 (M + 1) |
| 76 | 3.80(s,6H), 3.84(s,3H), 5.77(s,1H) 7.18~7.48(m,6H), 8.24(s,1H) | 444 (M + 1) |
| 77 | 1.43(t,6H), 3.80(s,6H), 4.08(q,2H), 5.77(s,1H) 6.94(d,2H), 7.20~7.45(m,3H), 7.63(d,2H), 8.20(s,1H) | 458 (M + 1) |
| 78 | 1.42(t,3H), 3.80(s,6H), 4.07(q,2H), 5.76(s,1H) 6.87~6.95(m,2H), 7.20~7.43(m,4H), 7.96(d,1H), 8.73(s,1H) | 458 (M + 1) |
| 79 | 3.79(s,6H), 5.77(s,1H), 7.00~7.50(m,12H), 8.23(s,1H) | |
| 80 | 0.98(t,3H), 1.51(m,2H), 1.78(m,2H), 2.80(s,6H) 4.00(m,2H), 5.77(s,1H), 6.90(d,2H), 7.21~7.45(m,3H), 7.63(d,2H), 8.20(s,1H) | 486 (M + 1) |
| 81 | 3.80(s,6H), 5.09(s(2H), 5.77(s,1H), 7.10(d,1H) 7.21~7.44(m,11H), 8.24(s,1H) | 520 (M + 1) |
| 82 | 3.80(s,6H), 5.11(s,2H), 5.77(s,1H) 6.98(d,2H), 7.20~7.43(m,8H), 7.63(d,2H), 8.21(s,1H) | 520 (M + 1) |
| 83 | 2.32(s,3H), 3.80(s,6H), 5.77(s,1H) 7.16~7.48(m,5H), 7.73(d,2H), 8.27(s,1H) | 472 (M + 1) |
| 84 | 3.79(s,6H), 5.77(s,1H) 7.21~7.64(m,7H), 8.23(s,1H) | 498 (M + 1) |
| 85 | 3.80(s,6H), 5.77(s,1H), 7.15~7.50(m,3H) 7.90(d,2H), 8.28(d,2H), 8.38(s,1H) | |
| 86 | 3.03(s,6H), 3.79(s,6H), 5.76(s,1H), 6.65(d,2H), 7.15~7.50(m,3H), 7.54(d,2H), 8.13(s,1H) | |
| 87 | 3.80(s,6H), 5.76(s,1H), 7.2~7.60(m,5H), 7.69(s,1H), 8.20(t,1H), 8.62(s,H) | 482 (M + 1) |
| 88 | 3.79(s,6H), 5.77(s,1H), 7.22~7.57(m,4H) 7.72(d,1H), 7.90(t,2H), 8.32(s,1H) | 482 (M + 1) |

TABLE (2-4)-continued

| Compd. No. | $^1$H NMR(CDCl$_3$) δ ppm | Mass (FAB) |
|---|---|---|
| 89 | 3.80(s,6H), 5.77(s,1H), 7.24~7.70(m,3H) 7.68(d,2H), 7.82(d,2H), 8.34(s,1H) | 482 (M + 1) |
| 90 | 3.80(s,6H), 3.94(s,3H), 5.77(s,1H), 7.22~7.50(m,3H), 7.79(d,2H), 8.09(d,2H), 8.33(s,1H) | 472 (M + 1) |
| 91 | 2.51(s,3H), 3.80(s,6H), 5.77(s,1H), 7.21(d,2H) 7.22~7.45(m,3H), 7.61(d,2H), 8.22(s,1H) | 460 (M + 1) |
| 92 | 3.80(s,6H). 5.78(s,1H), 7.20~7.45(m,3H), 7.72(d,2H), 7.83(d,2H), 8.33(s,1H) | 439 (M + 1) |
| 93 | 3.80(s,6H), 5.78(s,1H), 7.22~7.61(m,6H), 8.21(s,1H) | 482 (M + 1) |
| 94 | 3.80(s,6H), 3.84(s,3H), 5.77(s,1H), 6.80(d,1H) 7.21~7.53(m,4H), 8.09(d,1H), 8.56(s,1H) | 524 (M + 1) |
| 95 | 3.81(s,6H), 5.77(s,1H), 7.06~7.45(m,6H), 8.59(s,1H) | 466 (M + 1) |
| 96 | 3.80(s,6H), 5.77(s,1H), 6.79~6.90(m,1H), 7.21~7.46 (m,5H), 8.43(s,1H) | 450 (M + 1) |
| 97 | 3.81(s,6H), 5.78(s,1H), 7.21~7.49(m,4H), 7.58(d,1H), 7.98(d,1H), 8.72(s,1H) | 482 (M + 1) |
| 98 | 3.81(s,6H), 5.77(s,1H), 7.22~7.48 (m,5H), 8.02(d,1H), 8.64(s,1H) | 482 (M + 1) |
| 99 | 3.80(s,6H), 5.78(s,1H), 7.22~7.84(m,6H), 8.24(s,1H) | 482 (M + 1) |
| 100 | 3.82(s,6H), 5.79(s,1H), 7.21~7.64(m,4H), 8.25(d,1H), 8.73(s,1H), 8.89(s,1H) | 493 (M + 1) |
| 101 | 3.77(s,6H), 3.85(s,3H), 3.88(s,3H), 5.97(s,1H) 6.99~7.58(m,6H), 8.63(s,1H) | 474 (M + 1) |
| 102 | 3.80(s,6H), 3.81(s,6H), 5.78(s,1H), 6.56(s,1H) 6.83 (d,2H), 7.71~7.45(m,3H), 8.19(s,1H) | 474 (M + 1) |
| 103 | 3.77(s,3H), 3.80(s,6H), 3.86(s,3H), 5.77(s,1H) 6.40(d,1H), 6.43(m,1H), 7.15~7.45(m,3H) 7.88(d,1H), 8.53(s,1H) | 474 (M + 1) |
| 104 | 3.73(s,6H), 3.82(s,6H), 5.74(s,1H), 6.81(d,1H) 7.01(m,1H), 7.14~7.45(m,4H), 8.13(s,1H) | 474 (M + 1) |
| 105 | 2.33(s,3H), 3.80(s,6H), 3.88(s,3H), 5.77(s,1H) 7.01~7.45(m,6H), 8.24(s,1H) | 502 (M + 1) |
| 106 | 3.80(s,6H), 5.77(s,1H), 6.03(s,2H), 6.80~7.06(m,2H), 7.20~7.42(m,4H), 8.16(s,1H) | 458 (M + 1) |

EXAMPLE 9

Synthesis of Compound No. 107 (Q=phenyl, R=OCH$_3$)

4.0 g of thioester compound (II-1) prepared in Preparation 1 and 1.5 g of oxime (III'-1) prepared in Preparation 12 were dissolved in 50 ml of methylene chloride, and 2.2 g of CuBr$_2$ was added in the reaction mixture as stirred at room temperature. After stir for another 1 hour, the mixture was filtered and then the solvent was distilled off under reduced pressure. The residue thus obtained was purified by silica gel column chromatography to obtain 3.7 g of the above identified compound (yield 90%).

EXAMPLE 10

Synthesis of Compound No. 108 (Q=phenyl, R=SCH$_3$)

4.0 g of thioester compound (II-1) prepared in Preparation 1 and 2.0 g of oxime (III'-18) prepared in Preparation 13 were dissolved in 50 ml of methylene chloride, and after 5 minutes, 2.2 g of $CuBr_2$ was added in the reaction mixture as stirred at room temperature. After stir for another 1 hour, the mixture was filtered and then the solvent was distilled off under reduced pressure. The residue thus obtained was purified by silica gel column chromatography to obtain 4.2 g of the above identified compound (yield 90%).

In the same manner as described in Example 9 or 10, the compound No. 109–139 were prepared, and the physical properties thereof are given below in Table (2-5)

TABLE (2-5)

| Compd. No. | $^1$H NMR(CDCl$_3$) δ ppm | Mass (FAB) |
|---|---|---|
| 107 | 3.80(s,6H), 3.95(s,3H), 5.77(s,1H), 7.15~7.50(m,6H), 7.70(d,2H), 8.28(s,1H) | 444 (M + 1) |
| 108 | 1.30(t,3H), 3.79(s,6H), 4.33(q,2H), 5.77(s,1H) 7.15~7.50(m,6H), 7.80(d,1H), 8.52(s,1H) | 458 (M + 1) |
| 109 | <Syn> 0.94(t,3H), 1.69(m,2H), 3.80(s,6H), 5.77(s,1H), 7.15~7.80(m,8H) <anti>1.02(t,3H) 1.80(m,2H), 3.76(s,6H), 5.73(s,1H) | 472 (M + 1) |
| 110 | 1.79(s,3H), 3.81(s,6H), 3.94(s,3H), 5.77(s,1H) 7.12~7.43(m,7H) | |
| 111 | <syn> 2.00(s,3H), 3.80(s,6H), 3.93(s,3H), 5.78(s,1H), 7.10~7.50(m,7H) <anti>2.03(s,3H) 3.78(s,6H), 4.00(s,3H), 5.71(s,1H), 7.10~7.50(m,7H) | |
| 112 | 2.38(s,3H), 3.80(s,6H), 3.93(s,3H), 5.77(s,1H) 7.20(d,2H), 7.21~7.50(m,3H), 7,59(d,2H) | |
| 113 | 1.20(t,3H), 2.60~2.69(q,2H), 3.80(s,6H), 3.95(s,3H), 5.77(s,1H), 7.15~7.50(m,7H) | |
| 114 | 3.80(s,6H), 3.82(s,3H), 5.76(s,1H), 6.90(d,2H) 7.15~7.50(m,3H), 7.64(d,2H) | |
| 115 | <syn> 3.80(s,1H), 4.00(s,3H), 5.77(s,1H), 7.15~7.75(m,3H) <anti> 3.76(s,1H), 4.04(s,3H), 5.74(s,1H) | |
| 116 | 3.80(s,3H), 3.94(s,3H), 5.77(s,1H), 7.15~7.60(m,5H), 7.78(d,2H) | |
| 117 | 3.80(t,3H), 4.02(s,3H), 5.76(s,1H), 7.05~7.50(m,5H), 7.65~7.80(m,2H) | |
| 118 | 1.38(t,3H), 2.33(s,3H), 3.75(s,6H), 4.37(q,2H), 5.72(s,1H), 7.10~7.50(m,7H) | 472 (M + 1) |
| 119 | 3.79(s,6H), 3.85(s,3H), 3.94(s,3H), 5.77(s,1H), 6.95(d,2H), 7.15~7.65(m,5H) | |
| 120 | 2.51(s,3H), 3.80(s,6H), 3.93(s,3H) 5.77(s,1H), 7.15~7.65(m,7H) | |
| 121 | 3.80(s,6H), 3.94(s,3H), 5.77(s,1H), 7.15~7.85(m,7H) | |
| 122 | 3.79(s,6H), 3.93(s,3H), 5.77(s,1H), 7.20~7.70(m,5H), 7.80(d,2H) | |
| 123 | 3.03(s,6H), 3.80(s,6H), 3.94(s,3H), 5.76(s,1H), 6.64(d,2H), 7.15~7.60(m,5H) | |
| 124 | 2.02(s,3H), 3.83(s,6H), 5.77(s,1H), 7.21~7.44(m,8H) | 46 (M + 1) |
| 125 | 1.30(t,3H), 2.08(q,2H), 3.80(s,6H), 5.77(s,1H), 7.15~7.80(m,3H) | |
| 126 | 3.80(s,6H), 5.74(s,1H), 7.18~7.48(m,13H) | |
| 127 | 1.78(s,3H), 2.24(s,3H), 3.82(s,6H), 5.77(s,1H), 7.12~7.43(m,7H) | 475 (M + 1) |
| 128 | 2.00(s,3H), 2.38(s,3H), 3.83(s,6H), 5.77(s,1H), 7.10~7.50(m,7H) | |
| 129 | 2.00(t,3H), 2.00(s,3H), 2.60~2.69(q,2H) 3.80(s,6H), 5.75(s,1H), 7.15~7.50(m,7H) | |
| 130 | 1.20(t,3H), 2.00(s,3H), | 488 (M + 1) |

TABLE (2-5)-continued

| Compd. No. | $^1$H NMR(CDCl$_3$) δ ppm | Mass (FAB) |
|---|---|---|
| | 2.60~2.69(q,2H) 3.80(s,6H), 5.75(s,1H), 7.15~7.50(m,7H) | |
| 131 | 2.02(s,3H), 3.80(s,6H), 5.77(s,1H) 7.24~7.70(m,5H), 7.82(d,2H) | |
| 132 | <Syn> 2.00(s,3H), 3.80(s,3H), 3.82(s,6H), 5.77(s,1H), 6.80~7.00(m,2H), 7.15~7.50 (m,5H) <anti> 1.92(s,3H), 5.76(s,1H) | |
| 133 | 2.00(s,3H), 3.80(s,6H), 3.85(s,3H), 5.77(s,1H), 6.91(d,2H), 7.15~7.50(s,1H) 7.65(d,2H) | |
| 134 | 2.02(s,3H), 3.81(s,6H), 5.76(s,1H), 7.15~7.85(m,7H) | |
| 135 | 1.95(s,3H), 3.74(s,6H), 5.77(s,1H), 7.10~7.40(m,7H) | 494 (M + 1) |
| 136 | 2.04(s,3H), 3.81(s,6H), 5.77(s,1H), 7.15~7.52(m,3H), 7.58(d,2H), 7.74(d,2H) | |
| 137 | 2.02(s,3H), 3.80(s,6H), 5.76(s,1H), 7.05~7.80(m,7H) | (M + 1) |
| 138 | 2.05(s,3H), 3.78(s,6H), 5.77(s,1H), 7.12~7.50(m,7H) | (M + 1) |
| 139 | 2.04(s,3H), 3.79(s,6H), 5.77(s,1H), 7.12~7.50(m,12H) | (M + 1) |

EXAMPLE 11

Synthesis of Compound No. 140 (Q=pyridyl, R=H)

4.0 g of thioester compound (II-1) prepared in Preparation 1 and 1.2 g of 3-pyridylaldehyde oxime (III-2) prepared in Preparation 4 were dissolved in 50 ml of methylene chloride, and 2.2 g of $CuBr_2$ was added in the reaction mixture as stirred at room temperature. After stir for another 1 hour, the mixture was filtered and then the solvent was distilled off under reduced pressure. The residue thus obtained was purified by silica gel column chromatography to obtain 3.7 g of the above identified compound (yield 90%).

EXAMPLE 12

Synthesis of Compound No. 141 (Q=2-furyl, R=H)

4.0 g of thioester compound (II-1) prepared in Preparation 1 and 1.1 g of 2-furylaldehyde oxime (III-3) prepared in Preparation 5 were dissolved in 50 ml of methylene chloride, and after 5 minutes, 2.2 g of $CuBr_2$ was added in the reaction mixture as stirred at room temperature. After stir for another 1 hour, the mixture was filtered and then the solvent was distilled off under reduced pressure. The residue thus obtained was purified by silica gel column chromatography to obtain 3.4 g of the above identified compound (yield 85%).

In the same manner as described in Example 11 or 12, the compound No. 142–149 were prepared, and the physical properties thereof are given below in Table (2-6)

TABLE (2-6)

| Compd. No. | $^1$H NMR(CDCl$_3$) δ ppm | Mass (FAB) |
|---|---|---|
| 140 | 3.80(s, 6H), 5.78(s, 1H), 7.20~7.50(m, 4H), 8.20(d, 1H), 8.38(s, 1H), 8.70~8.90(br,2H) | |
| 141 | 3.80(s, 6H), 5.76(s, 1H), 6.52(s, 1H), 6.91(d, 1H), 7.15~7.50(m, 3H), 7.58(s, 1H), 8.20(s, 1H) | 449 (M + 1) |

TABLE (2-6)-continued

| Compd. No. | $^1$H NMR(CDCl$_3$) δ ppm | Mass (FAB) |
|---|---|---|
| 142 | 3.80(s, 6H), 5.77(s, 1H), 6.86(s, 1H), 7.20–7.46(m, 4H), 7.76(s, 1H), 8.25(s, 1H) | 404 (M + 1) |
| 143 | 3.82(s, 6H), 5.79(s, 1H), 7.22–7.48(m, 5H), 8.28(s, 1H) | 449 (M + 1) |
| 144 | 2.37(s, 3H), 3.81(s, 6H), 5.77(s, 1H), 6.13(d, 1H), 6.78(d, 1h), 7.19–7.46(m, 3H), 8.08(s, 1H) | 418 (M + 1) |
| 145 | 3.80(s, 6H), 5.77(s, 1H), 7.10–7.52(m, 6H), 8.44(s, 1H) | 420 (M + 1) |
| 146 | 3.80(s, 6H), 5.77(s, 1H), 7.15–7.50(m, 6H), 7.53(d, 1H), 7.69(d, 1H), 8.33(s, 1H) | 420 (M + 1) |
| 147 | 2.51(s, 3H), 5.79(s, 6H), 5.77(s, 1H), 6.75(d, 1H), 7.17–7.46(m, 4H), 8.32(s, 1H), | 434 (M + 1) |
| 148 | 3.81(s, 6H), 5.79(s, 1H), 7.22–7.50(m, 4H), 7.87(d, 1H), 8.40(s, 1H) | 465 (M + 1) |
| 149 | 3.80(s, 6H), 3.85(s, 3H), 5.77(s, 1H), 6.17(t, 1H), 6.52(d, 1H), 6.80(d, 1H), 7.20–7.42(m, 4H), 9 ⅲ 8.12(s, 1H) | 417 (M + 1) |

EXAMPLE 13

Synthesis of Compound No. 154 (Q=2-methyl-5-furyl, R=SCH$_3$)

4.0 g of thioester compound (II-1) prepared in Preparation 1 and 1.4 g of oxime (III-19) prepared in Preparation 8 were dissolved in 50 ml of methylene chloride, and 2.2 g of CuBr$_2$ was added in the reaction mixture as stirred at room temperature. After stir for another 1 hour, the mixture was filtered and then the solvent was distilled off under reduced pressure. The residue thus obtained was purified by silica gel column chromatography to obtain 3.7 g of the above identified compound (yield 90%).

EXAMPLE 14

Synthesis of Compound No. 160 (Q=2-thienyl, R=CH$_3$, Syn) and No. 161 (Q=2-thienyl, R=CH$_3$, Anti)

4.0 g of thioester compound (II-1) prepared in Preparation 1 and 1.4 g of oxime (III-9) prepared in Preparation 6 were dissolved in 50 ml of methylene chloride, and after 5 minutes 2.2 g of CuBr$_2$ was added in the reaction mixture as stirred at room temperature. After stir for another 1 hour, the mixture was filtered and then the solvent was distilled off under reduced pressure. The residue thus obtained was purified by silica gel column chromatography to obtain 3.0 g of the above identified syn-isomer (yield 80%) and 0.7 g of anti-isomer (yield 18%).

In the same manner as described in Example 13 or 14, the compound No. 150–172 were prepared, and the physical properties thereof are given below in Table (2-7)

TABLE (2-7)

| Compd. No. | $^1$H NMR(CDCl$_3$) δ ppm | Mass (FAB) |
|---|---|---|
| 150 | 2.21(s, 2H), 3.90(s, SH), 5.79(s, 1H) 7.20–7.50(m, 4H), 8.21(d, 1H), 8.8(br,2H) | |
| 151 | <Syn>2.23(s.3H), 3.80(s, Sh), 5,75(s, 1H), 6,50(br,1H), 6.91(s, 1H), 7.15–7.50(m, 2H), (s, 1H)<anti> 2.09(s, 3H), 3,77(s, 6H), 9.71s, 1H) | 418 (M + 1) |
| 152 | 2.20(s, 3H), 2.36(s, 3H), 3.80(s, 6H), 5.76 5.76(s, 1H), 6.10(d, 1H), 6.78(d, 1H) 7.15–7.50(m, 3H) | 432 (M + 1) |
| 153 | 2.24(s, 3H), 3.80(s, 6H), 5.77(s, 1H) 6.15(d, 1H), 7.00–7.50(m.4H) | |
| 154 | 2.34(s, 3H), 2.36(s, 3H), 3.78(s, 6H), 5.75(s, 1H), 6.05(d, 1H), 6.78(d, 1H) 7.15–7.50(m, 3H) | 464 (M + 1) |
| 155 | 2.34(s, 3H), 3.80(s, 6H), 4.01(s, 3H), 5.77(s, 1H), 6.08(d, 1H), 6.86(d, 1H) 7.15–7.50(m, 3H) | 448 (M + 1) |
| 156 | 2.26(s, 3H), 3.78(s, 6H), 4.00(s, 3H), 5.73(s, 1H),6.03(d, 1H), 7.13(d, 1H) 7.15–7.50(m, 3H) | 448 (M + 1) |
| 157 | 2.35(s, 3H), 3.80(s, 6H), 5.76(s, 1H), 7.15–7.50(m, 3H) | |
| 158 | 2.15(s, 3H), 2.22(s, 3H), 2.38(s, 3H), 3.79(s, 6H), 5.76(s, 1H), 6.04(s, 1H) 7.15–7.50(m, 3H) | |
| 159 | <Syn>3.78(s, 6H), 3.97(s, 3H), 5,77(s, 1H) 6.51(br,1H), 7.21–7.63(m, 5H) <anti>3.81(s, 6h), 3.92(s, 3H), 5.72(s, 1H) | 462 (M + 1) |
| 160 | 2.33(s, 3H), 3.80(s, 6H), 5.77(s, 1H), 7.07(t, 1H), 7.15–7.50(m, SH) | 434 (M + 1) |
| 161 | 2.49(s, 3H), 3.76(s, 6H), 5.70(s, 1H), 7.05(t.1H), 7.15–7.55(m, SH) | 434 (M + 1) |
| 162 | 2.29(s, 3H), 3.80(s, 6H), 5.76(s, 1H), 7.15–7.50(m, 3H), 7.70(s, 1H) | 434 (M + 1) |
| 163 | 3.77(s, 6H), 3.93(s, 6H), 5.73(s, 1H), 7.09(t, 1H), 7.15–7.7.55(m, 3H), 7.63(d, 1H), 7.92(d, 1H) | 478 (M + 1) |
| 164 | <Syn>3.81(s, SH), 3.81(s.1H) 7.10–8.10(m, SH), <anti, 3.76(s, SH) 3.95(s, SH), 5.72(s, SH) | 478 (M + 1) |
| 165 | 2.26(s, 3H), 3.79(s, 6H), 5.76(s, 1H), 6.85(d, 1H), 7.15–7.50(m, 3H) | |
| 166 | 2.43(s, 3H), 3.78(s, 6H), 5.71(s, 1H), 6.90(d, 1H), 7.28(d, 1H), 7.15–7.50(m, 3H) | |
| 167 | 2.32(s, 3H), 2.36(s, 6H), 3.79(s, 6H), 5.75(s, 1H), 6.88(d.1H), 7.15–7.50(m, 4H) | 448 (M + 1) |
| 168 | 2.33(s, 3H), 2.51(s, 3H), 3.80(s, SH), 5.77(s, 1H), 6.73(s, 1H) 7.15–7.50(m, 3H) | 448 (M + 1) |
| 169 | 2.19(s, 3H), 2.38(s, 3H), 2.45(s, 3H), 3.80(s, SH), 5.77(s, 1H), 6.70(s, 1H) 7.15–7.50(m, 3H) | 462 (M + 1) |
| 170 | 2.36(s, 3H), 2.82(s, 3H), 3.80(s, 6H), 5.77(s, 1H), 6.68(s, 1H), 7.15–7.50(m, 4H) | 480 (M + 1) |
| 171 | 2.19(s, 3H), 3.65(s, 3H), 3.80(s, 6H), 5.76(s.1H), 645–6.60(m, 2H), 7.08(s, 1H) 7.15–7.50(m, 3H) | |
| 172 | 2.29(s, 3H), 3.82(s, 3H), 3.77(s, SH), 5.70(s, 1H), 6.40–6.55(m.2H), 7.15–7.50(m, 4H) | |

EXAMPLE 15

Synthesis of Compound No. 175 (Q=phenyl, R=CN)

4.0 g of thioester compound (II-1) prepared in Preparation 1 and 1.4 g of oxime (III-20) prepared in Preparation 9 were dissolved in 100 ml of xylene, and stirred for 30 minutes under reflux of xylene. the solvent was distilled off under reduced pressure. The residue thus obtained has purified by silica gel column chromatography to obtain 0.8 g of the above identified compound (yield 20%).

$^1$H NMR (CDCl$_3$, δ): 3.81(s, 6H), 5.78(s, 1H), 7.27(d, 1H), 7.39(d, 1H), 7.45–7.65(m, 4H), 7.94(d, 2H); Mass-(FAB): 439(M+1).

EXAMPLE 16

Synthesis of Compound No. 179 (Q=p-methoxyphenyl, R=CN)

4.0 g of thioester compound (II-1) prepared in Preparation 1 and 1.6 g of oxime (III-21) prepared in Preparation 10 were dissolved in 50 ml of methylene chloride, and 2.2 g of CuBr$_2$ was added in the reaction mixture as stirred at room temperature. After stir for another 1 hour, the mixture was filtered and then the solvent was distilled off under reduced pressure. The residue thus obtained was purified by silica gel column chromatography to obtain 4.0 g of the above identified compound (yield 90%).

$^1$H NMR (CDCl$_3$, δ): 3.80(s, 6H), 3.88(s, 3H), 5.78(s, 1H), 6.98(d, 2H), 7.15–7.50(m, 3H), 7.89(d, 2H; Mass-(FAB): 469(M+1).

In the same manner as described in Example 15 or 16, the compound No. 173–184 were prepared, and the physical properties thereof are given below in Table (2-6)

TABLE (2-8)

| Compd. No. | $^1$H NMR(CDCl$_3$) δ ppm | Mass (FAB) |
|---|---|---|
| 173 | 3.80(s, 6H), 5.77(s, 1H), 7.5–7.55(m, 3H) | |
| 174 | 3.80(s, 6H), 5.76(s, 1H), 7.15–7.55(m, 3H) | |
| 175 | 3.81(s, 6H), 5.78(s, 1H), 7.27(d, 1H), 7.39(d, 1H), 745–18 7.66(m, 4H), 7.94(d, 2H) | 439 (M + 1) |
| 176 | 2.50(s, 3H), 3.80(s, 6H), 5.78(s, 1H), 7.15–7.70(m, 7H) | 453 (M + 1) |
| 177 | 2.40(s, 3H), 3.79(s, 6H), 5.77(s, 1H), 7.28(d, 1H), 7.35–7.50(m, 4H), 7.60–7.70(d, 2H) | 453 (M+ 1) |
| 178 | 2.41(s, 3H), 3.80(s, 6H), 5.77(s, 1H), 7.20–7.55(m, 5H), 7.81(d, 2H) | 453 (M + 1) |
| 179 | 3.80(s, 6H), 3.88(s, 3H), 5.78(s, 1H), 6.98(d, 2H), 7.15–7.50(m, 3H), 7.89(d, 2H) | 469 (M + 1) |
| 180 | 1.43(t, 3H), 3.80(s, 6H), 4.12(q, 2H), 6.98(d, 2H), 7.20–7.50(m, 5H), 7.75(d, 2H) | 483 (M + 1) |
| 181 | 1.25(t, 3H), 2.72(q, 2H), 3.80(s, 6H), 5.77(s, 1H), 7.15–7.50(m, 5H), 7.83(d, 2H) | 467 (M + 1) |
| 182 | 3.78(s, 6H), 5.76(s, 1H), 7.15–7.55(m, 5H), 7.84(d, 2H) | 473 (M + 1) |
| 183 | 3.80(s, 6H), 5.78(s, 1H), 7.15–7.55(m, 5H), 7.88(d, 2H) | 473 (M + 1) |
| 184 | 3.78(s, 6H), 5.76(s, 1H), 7.05–7.73(m, 7H) | 457 (M + 1) |

EXAMPLE 17

Synthesis of Compound No. 186 (Q=H, R=H)

848 mg of thioester compound (II-1) prepared in Preparation 1 was dissolved in 5 ml of methylene chloride, and 470 mg of CuBr$_2$ was added in the reaction mixture as stirred at room temperature. After stir for another 30 minutes, 298 mg of 2-isonitroso acetophenone was added into the reaction mixture, and stirred again for 30 minutes. The solvent was distilled off under reduced pressure. The residue thus obtained was purified by silica gel column chromatography to obtain 750 mg of the above identified compound (yield 85%).

In the similar manner as described in Example 17, the compound No. 187–194 were prepared and, and the physical properties thereof are given below in Table (2-9)

TABLE (2-9)

| Compd. No. | $^1$H NMR(CDCl$_3$) δ ppm | Mass (FAB) |
|---|---|---|
| 186 | 3.81(s, 6H), 5.79(s, 1H), 7.24(d, 1H), 7.37(d, 1H), 7.48(t, 3H), 7.62(t, 1H), 8.01(s 1H), 8.15(d, 2H) | 442 (M + 1) |
| 187 | 2.23(s, 3H), 3.81(s, 6H), 5.79(s, 1H), 7.21–7.47(m, 5H), 7.59(t, 1H), 8.05(d, 2H) | 456 (M + 1) |
| 188 | 0.92(t, 3H), 1.48–1.63(m, 2H), 2.72(t, 2H), 3.80(s, 6H), 5.79(s, 1H), 7.23(d, 1H), 7.34–7.47(m, 4H), 7.59(t, 1H), 8.04(d, 2H) | 484 (M + 1) |
| 189 | 0.86(t, 3H), 1.23–1.38(m, 2H), 1.42–1.55(m, 2H), 2.73(t, 2H), 3.80(s, 6H), 5.79(s, 1H), 7.22(d, 1H), 7.34–7.48(m, 4H) 7.58(t, 1H), 8.03(d, 2H) | 498 (M + 1) |
| 190 (E:Z=5:1) | <E> 3.79(s, 6H), 5.77(s, 1H), 7.04–8.10(m, 13H), <Z> 3.71(s, 6H), 5.74(s, 1H), 7.04–8.10(m, 13H), | 518 (M + 1) |
| 191 | 3.81(s, 6H), 5.79(s, 1H), 7.20–8.20(m, 8H), | 520 (M + 1) |
| 192 | 2.33(s, 3H), 3.81(s, 6H), 5.79(s, 1H), 7.20–8.10(m, 7H) | 474 (M + 1) |
| 193 | 3.82(s, 6H), 5.80(s, 1H), 7.25(d, 1H), 7.36–7.52(m, 4H), 7.65(t, 1H), 8.08(d, 2H) | 476 (M + 1) |
| 194 | 2.18(s, 3H), 3.84(s, 6H), 5.79(s, 1H), 7.22–7.55(m, 5H), 7.68(t, 1H), 8.05(d, 2H) | 488 (M + 1) |

EXAMPLE 18

Synthesis of Compound No. 186 (Q=H, R=H)

848 mg of thioester compound (II-1) prepared in Preparation 1 was dissolved in 5 ml of methylene chloride, and 470 mg of CuBr$_2$ was added in the reaction mixture as stirred at room temperature. After stir for another 30 minutes, inner reactor was cooled down to −15° C. and then 481 mg of α-benzoyl-α-anilino oxime was added in the reaction mixture, stirred for 1 hour. The the mixture was filtered and condenced. The residue thus obtained was purified by silica gel column chromatography to obtain 638 mg of the above identified compound (yield 60%).

In the similar manner as described in Example 18, the compound No. 195–204 were prepared and, and the physical properties thereof are given below in Table (2-10)

TABLE (2-10)

| Compd. No. | $^1$H NMR(CDCl$_3$) δ ppm | Mass (FAB) |
|---|---|---|
| 195 | 3.71(s, 6H), 5.71(s, 1H), 6.60 (br, 1H), 6.88–8.08(m, 13H) | 533 (M + 1) |
| 196 | 3.78(s, 6H), 4.37(d, 2H), 5.76 (s, 1H), 5.70(t, 1H), 7.17–8.05(m, 13H) | 547 (M + 1) |
| 197 | 3.69(s, 3H), 3.76(s, 6H), 4.34(d, 2H), 5.74(s, 1H), 5.94(t, 1H), 6.78–8.05(m, 12H) | 577 (M + 1) |
| 198 | 3.73(s, 3H), 3.78(s, 6H), 4.35(d, 2H), 5.75(s, 1H), 5.81(t, 1H), 6.72–8.07(m, 12H) | 577 (M + 1) |
| 199 | 3.74(s, 3H), 3.78(s, 6H), 4.30(d, 2H), | 577 (M + 1) |

TABLE (2-10)-continued

| Compd. No. | $^1$H NMR(CDCl$_3$) δ ppm | Mass (FAB) |
|---|---|---|
|  | 5.73(t, 1H), 5.76(s, 1H), 6.75–8.05(m, 12H) |  |
| 200 | 2.23(s, 3H), 3.76(s, 6H), 4.39(d, 2H), 5.63(t, 1H), 5.73(s, 1H), 7.08–8.07(m, 12H) | 561 (M + 1) |
| 201 | 2.30(s, 3H), 3.80(s, 6H), 4.36(d, 2H), 5.77(t, 1H), 5.78(s, 1H), 7.08–8.08(m, 12H) | 561 (M + 1) |
| 202 | 3.77(s, 6H), 4.48(d, 2H), 5.73(s, 1H), 5.93(t, 1H), 7.14–8.07(m, 12H) | 581 (M + 1) |
| 203 | 3.78(s, 6H), 4.37(d, 2H), 5.76(s, 1H), 5.83(t, 1H), 7.11–8.05(m, 12H) | 581 (M + 1) |
| 204 | 3.80(s, 6H), 4.41(d, 2H), 5.78(s, 1H), 5.79(t, 1H), 6.09(d, 1H), 6.18(t, 1H), 7.19–8.05(m, 9H) | 537 (M + 1) |

EXAMPLE 19

Synthesis of Compound No. 186 (Q=H, R=H)

848 mg of thioester compound (II-1) prepared in Preparation 1 was dissolved in 5 ml of methylene chloride, and 470 mg of CuBr$_2$ was added in the reaction mixture as stirred at room temperature. After stir for another 30 minutes, 266 mg of methyl N-hydroxybutylthioimidate was added in the reaction mixture and stirred for 20 minutes. The mixture was filtered and condenced. The residue thus obtained was purified by silica gel column chromatography to obtain 775 mg of the above identified compound (yield 91%).

In the similar manner as described in Example 19, the compound No. 205–219 were prepared, and the physical properties thereof are given below in Table (2-11)

TABLE (2-11)

| Compd. No. | $^1$H NMR(CDCl$_3$) δ ppm | Mass (FAB) |
|---|---|---|
| 205 | 0.99(t, 3H), 1.60–1.68(m, 2H), 2.30 (s, 3H), 2.52(t, 2H), 3.81(s, 6H), 5.75(s, 1H), 7.16–7.41(m, 3H) | 426 (M + 1) |
| 206 | 0.93(t, 3H), 132–1.46(m, 2H), 156–1.67(m, 2H), 2.30(s, 3H), 2.54(t, 2H), 3.81(s, 6H), 5.75(s, 1H), 7.16–7.41(m, 3H) | 440 (M + 1) |
| 207 | 1.30(t, 3H), 2.00(s, 3H), 3,81 (s, 6H), 4.19(q, 2H), 5.77(s, 1H), 7.17–7.44(m, 3H) | 396 (M + 1) |
| 208 | 2.38(s, 3H), 2.54(s, 3H), 3.81 (s, 6H), 5.77(s, 1H), 7.17–7.44 (m, 3H) | 430 (M + 1) |
| 209 | 3.45(s, 4H), 3.81(s, 6H), 5.73 (s, 1H), 7.13–7.39(m, 3H) | 428 (M + 1) |
| 210 | 0.79(t, 3H), 1.32–1.46(m, 2H), 2.33(t, 2H), 3.69(s, 6H), 5.63(s, 1H), 6.96(s, 1H), 7.02–7.42(m, 8H) | 471 (M + 1) |
| 211 (E:Z=5:2) | <E> 0.74(t, 3H), 1.12–1.39 (m, 2H+2H), 2.32(t, 2H), 3.69 (s, 6H), 5.64(s, 1H), 6.97(s, 1H), 7.05–7.40(m, 8H), <Z> 0.88(t, 3H), 1.25–1.66 (m, 2H+2H), 2.48(t, 2H), 3.79 (s, 6H), 5.76(s, 1H), 6.97(s, 1H), 7.05–7.40(m, 8H) | 485 (M + 1) |
| 212 (E:Z=3:1) | <E> 0.95(t, 3H), 1.56–1.68 (m, 2H), 2.26(t, 2H), 3.74 (s, 6H), 4.33(d, 2H), 5.54(t, 1H), 5.70(s, 1H), 7.08–7.37(m, 8H), <Z> 0.91(t, 3H), 1.52–1.64 | 485 (M + 1) |

TABLE (2-11)-continued

| Compd. No. | $^1$H NMR(CDCl$_3$) δ ppm | Mass (FAB) |
|---|---|---|
|  | (m, 2H), 2.31(t, 2H), 3.81 (s, 6H), 4.36(d, 2H), 5.54(t, 1H), 5.77(s, 1H), 7.08–7.37(m, 8H) |  |
| 213 (E:Z=3:1) | <E> 0.88(t, 3H), 1.41–1.62 (m, 2H+2H), 2.28(t, 2H), 3.74 (s, 6H), 4.33(d, 2H), 5.55(t, 1H), 5.70(s, 1H), 7.11–7.39(m, 8H), <Z> 0.88(t, 3H), 1.41–1.62 (m, 2H+2H), 2.34(t, 2H), 3.81 (s, 6H), 4.34(d, 2H), 5.56(t, 1H), 5.77(s, 1H), 7.11–7.39(m, 8H) | 499 (M + 1) |
| 214 | 1.99(s, 3H), 3.32(t, 4H), 3.71(t, 4H), 3.81(s, 6H), 5.77(s, 1H), 7.15–7.41(m, 3H) | 437 (M + 1) |
| 215 | 0.91(s, 3H), 1.44–1.57(m, 2H), 2.41(t, 2H), 3.32(t, 4H), 3.71(t, 4H), 3.80(s, 6H), 5.77(s, 1H), 7.16–7.39(m, 3H) | 465 (M + 1) |
| 216 | 0.86(s, 3H), 1.25–1.52(m, 2H+2H), 2.43(t, 2H), 3.32(t, 4H), 3.71(t, 4H), 3.80(s, 6H), 5.77(s, 1H), 7.16–7.38(m, 3H) | 479 (M + 1) |
| 217 | 3.41(s, 3H), 3.79(s, 6H), 5.68(s, 1H), 6.54(s, 1H), 7.14–7.50(m, 8H) | 499 (M + 1) |
| 218 | 1.98(s, 3H), 3.71(s, 6h), 5.30(s, 1H), 5.69(s, 1H), 6.98–7.41(m, 8H) | 499 (M + 1) |
| 219 | 3.50(s, 3H), 3.80(s, 6H), 5.77(s, 1H), 6.93–7.45(m, 7H) | 473 (M + 1) |

The imino-ester type compounds of the present invention are not pre-herbicides but excellent herbicidal ALS inhibitors in themselves, and exhibit markedly higher herbicidal activities as compared with known compounds disclosed in the aforementioned publications and literatures, at a relatively low dose not only against annual weeds but also against perennial weeds, and at the same time, they have a high level of safety against crop plants such as cotton (*Gossypium hirsutum*), rice plant (*Oryza sativa*), wheat (*Triticum aestivum*) or soybean (*Glycine max*), and are effective not only the major weeds grown such crop plant fields but also against generally hardly controllable weeds. The compounds of the present invention have a feature that their toxicity against human beings and animals is very low while their herbicidal activities are extremely high.

The compounds and the herbicidal compositions of the present invention are capable of effectively controlling weeds grown in upland fields such as crabgrass (*Digitaria sanguinalis*), giant foxtail (*Sataria farberii*), barnyardgrass (*Echinochloa crus-galli* var. *caudata*), shattercane (*Sorghum bicolor*), *Aeschynomene indica*, *Solanum nigrum*, velvet leaf (*Abutilon theophrasti*), *Calystegia japonica* and weeds grown in paddy fields such as *Echinochloa crus-galli* var. *eryziccia*, *Aneilema kaisak*, *Scirpus jumcoides*, monochoria (*Monochoria varinalis*), flatsedge (*Cyperus difformis*), *Potamogeton distinnctus*, *Sagittaria trifolia*, *Eleocharis kuroguwai*, *Sagittaria pygmaea*. Thus, these weeds and crop plants such as cotton (*Gosshipium hirsutum*) and rice plant (*Oryxa sativar*) will be used to determine the herbicidal effects of the compounds according to the present invention.

The herbicidal composition of the present invention comprises a herbicidally effective amount of a 6-chloro-2-(4,6-dimethoxypyrimidin-2-yl)oxybenzoic acid imino ester derivatives of the present invention and an agricultural carrier or adjuvant. When the compound of the present invention is used as a herbicide, the compound may be used as it is or as formulated in various formulations such as a wettable powder, a granule, an emulsifiable concentrate or a dust by blending it with a carrier, a surfactant, a dispersing agent or an adjuvant which is commonly employed for the formulation of agricultural chemicals.

As the carrier to be used for the formulation, there may be mentioned a solid carrier such as jeeklite, talc, bentonite, clay, kaolin, diatomaceous earth, white carbon, vermiculite, slaked lime, silica sand, ammonium sulfate or urea, or a liquid carrier such as isopropyl alcohol, xylene, cyclohexane or methyl naphthalene. As the surfactant and dispersing agent, there may be aryl ether or a polyoxyethylene sorbitol mono-alkylate. As the adjuvant, for example, carboxymethyl cellulose, polyethylene glycol or gum arabic may be mentioned. In practical use, such a herbicide may be diluted to a suitable concentration before application, or may directly be applied.

The herbicide of the present invention may be used in combination with other herbicides.

The herbicide of the present invention is capable of controlling various weeds in a paddy field by irrigated soil treatment before or after the emergence of weeds. Further, the herbicide is capable of controlling various weeds in an upland field by soil treatment before or after the emergence of weeds or by foliage treatment.

The dose of the active ingredient varies depending upon the field to be treated i.e. whether it is an agricultural field or non-agricultural field, the type of treatment, i.e. whether it is soil treatment or foliage treatment, the crop plants to be protected and the weeds to be killed. However, it is usually within a range of from 0.001 to 50 g/10 a, preferably from 0.01 to 20 g/10 a.

For instance, for soil treatment for an upland agricultural field, the dose of the active ingredient is usually from 0.005 to 20 g/10 a, although it depends on the crop plant and weeds to be killed.

For foliage treatment for an upland agricultural field, the dose is usually from 0.001 to 10 g/10 a. In the case of a non-agricultural field, the dose is usually from 0.05 to 50 g/10 a for soil or foliage treatment.

Now, Formulation Examples for the herbicidal composition of the present invention will be given. However, it should be understood that the present invention is by no means restricted to these specific Examples. In these Examples, '%' means '% by weight'.

FORMULATION EXAMPLE 1

Upland Field Condition, (16 g,ha)

5 mg of the compound of this invention was dissolved in 640 ml of organic solvent (acetone), and then diluted with 640 ml of distilled water, which contains 0.2% of tween 20, or non-ionic surface, to obtain an emulsifiable concentrate.

FORMULATION EXAMPLE 2

Paddy Field Condition, (16 g/ha)

5 mg of the compound of this invention was dissolved in 320 ml of organic solvent (acetone), and then diluted with 320 ml of distilled water, which contains 0.2% of non-=ionic surfactant, or tween 20, to obtain an emulsifiable concentrate.

The determination of the herbicidal effects of the novel herbicides of the present invention was carried out by using pot-treatment and cultivation of test plants (weeds and crop plants) in greenhouse. And, the herbicidal activity on the weeds and phytotoxicity to crop plants were evaluated by observing the overground segments of the weeds and crop plants in accordance with the standard as identified in the following Table 3.

TABLE 3

| Evaluation Standards of Herbicidal Activity and Phytoxicity | | |
|---|---|---|
| Index No. | Herbicidal Activity | Phytoxicity |
| 0 | 0% | 0% |
| 1 | 10–20% | 10–20% |
| 2 | 30–40% | 30–40% |
| 3 | 50–60% | 50–60% |
| 4 | 70–80% | 70–80% |
| 5 | 90–100% | 90–100% |

TEST EXAMPLE 1

Soil Treatment before the Emergence of Weeds in Upland

Squarish plastic pots (20×15×10 cm) were filled with upland field soil (sterilized sandy-loam, pH 5.5–6.0), and then, in a 300 cm² pot filled with soil, seeds of cotton were sown, and seeds of 8 sorts of weeds grown in upland field were sown separately in a different pot, and covered with soil of a thickness of 0.5 cm. For the soil treatment, a predetermined amount (12 ml per each pot) of an emulsifiable concentrate prepared in accordance with Formulation Example 1 was uniformly applied to the soil surface one day after the plantation. The evaluation was conducted on the 30th day after the treatment with the herbicide. The results were evaluated in accordance with the standards as identified in Table 3 and shown by the index numbers in Table 4. Note 1. The abbreviations of the tested plants are as follows (the same abbreviations are used in othertables).

| | |
|---|---|
| Gos: | cotton (*Gosshipium hirsutum*) |
| Cal: | *Calystegia japonica* |
| Sol: | *Solanum nigrum* |
| Abu: | velvet leaf (*Abutilon theophrasti*) |
| Aes: | *Aeschynomena indica* |
| Dig: | crabgrass (*Digitaria sanquinalis*) |
| Sat: | giant foxtail (*Sataria farberii*) |
| Ech: | barnyardgrass (*Echinochloa crusgalli* var. *caudata*) |
| Sor: | shattercane (*Sorghum bicolor*) |

TABLE 4

| Comd. No. | Dose (g/ha) | Cotton | Broadleaf Weeds | | | | Narrowleaf Weeds | | | |
|---|---|---|---|---|---|---|---|---|---|---|
| | | | Cal | Sol | Abu | Aes | Dig | Sat | Ech | Sor |
| 1 | 16 | 0 | 5 | 4 | 4 | 4 | 3 | 5 | 2 | 5 |
| 2 | 16 | 0 | 5 | 5 | 5 | 5 | 4 | 4 | 4 | 5 |
| 3 | 16 | 1 | 4 | 4 | 4 | 4 | 5 | 4 | 4 | 5 |
| 4 | 16 | 0 | 5 | 4 | 5 | 4 | 4 | 3 | 3 | 5 |
| 5 | 16 | 1 | 5 | 5 | 4 | 4 | 4 | 4 | 4 | 5 |
| 6 | 16 | 0 | 4 | 4 | 5 | 4 | 4 | 4 | 3 | 5 |
| 7 | 16 | 0 | 4 | 5 | 5 | 4 | 3 | 4 | 3 | 4 |
| 8 | 16 | 1 | 5 | 5 | 5 | 5 | 5 | 5 | 5 | 5 |
| 9 | 16 | 1 | 4 | 4 | 4 | 4 | 4 | 4 | 4 | 5 |
| 10 | 16 | 2 | 5 | 4 | 4 | 4 | 5 | 4 | 4 | 5 |
| 11 | 16 | 0 | 5 | 4 | 4 | 4 | 5 | 5 | 5 | 5 |
| 12 | 8 | 0 | 5 | 4 | 4 | 4 | 4 | 4 | 4 | 5 |
| 13 | 16 | 0 | 5 | 5 | 5 | 4 | 5 | 5 | 5 | 5 |
| 14 | 16 | 1 | 5 | 4 | 4 | 4 | 4 | 5 | 4 | 5 |
| 15 | 16 | 0 | 5 | 4 | 4 | 4 | 5 | 4 | 5 | 5 |
| 16 | 16 | 2 | 5 | 5 | 5 | 5 | 5 | 5 | 5 | 5 |
| 17 | 16 | 2 | 5 | 4 | 4 | 5 | 5 | 5 | 4 | 5 |
| 18 | 16 | 2 | 5 | 4 | 3 | 5 | 4 | 5 | 5 | 2 |
| 19 | 16 | 0 | 5 | 4 | 5 | 3 | 4 | 5 | 4 | 5 |
| 20 | 16 | 0 | 5 | 5 | 5 | 4 | 3 | 4 | 4 | 5 |
| 21 | 16 | 1 | 4 | 4 | 2 | 4 | 4 | 4 | 4 | 2 |
| 22 | 16 | 0 | 5 | 5 | 4 | 5 | 4 | 4 | 5 | 5 |
| 23 | 16 | 2 | 5 | 5 | 5 | 5 | 5 | 5 | 5 | 5 |
| 24 | 16 | 1 | 5 | 5 | 4 | 4 | 5 | 5 | 4 | 5 |
| 25 | 16 | 2 | 5 | 4 | 3 | 4 | 5 | 5 | 5 | 2 |
| 26 | 16 | 2 | — | 5 | 0 | 2 | 5 | 4 | 5 | 3 |
| 27 | 16 | 1 | 4 | 4 | 5 | 5 | 4 | 5 | 4 | 5 |
| 28 | 16 | 0 | 5 | 4 | 5 | 5 | 4 | 4 | 5 | 5 |
| 29a | 16 | 0 | 5 | 5 | 4 | 5 | 5 | 4 | 4 | 5 |
| 29b | 16 | 2 | 4 | 4 | 4 | 4 | 4 | 4 | 4 | 4 |
| 30 | 16 | 1 | 4 | 5 | 4 | 5 | 5 | 5 | 5 | 5 |
| 31a | 16 | 0 | 5 | 4 | 3 | 3 | 3 | 2 | 3 | 5 |
| 31b | 16 | 2 | 4 | 4 | 3 | 3 | 3 | 3 | 3 | 4 |
| 32 | 16 | 0 | 5 | 4 | 4 | 3 | 2 | 4 | 3 | 5 |
| 33 | 16 | 1 | 5 | 4 | 3 | 3 | — | 3 | 3 | 5 |
| 34 | 16 | 0 | 4 | 4 | 2 | 2 | — | 1 | 2 | 4 |
| 35 | 16 | 0 | 5 | 5 | 5 | 4 | 4 | 5 | 5 | 5 |
| 36 | 16 | 0 | 2 | 4 | 4 | 3 | 1 | 4 | 4 | 5 |
| 37 | 16 | 0 | 5 | 4 | 3 | 3 | 4 | 4 | 3 | 5 |
| 38 | 16 | 0 | 4 | 4 | 3 | 4 | 2 | 3 | 2 | 4 |
| 39 | 16 | 0 | 4 | 4 | 2 | 3 | 3 | 3 | 4 | 4 |
| 40 | 16 | 2 | 4 | 4 | 3 | 4 | 3 | 3 | 3 | 4 |
| 41 | 16 | 0 | 5 | 4 | 2 | 3 | — | 2 | 1 | 4 |
| 58 | 16 | 0 | 5 | 4 | 4 | 4 | 5 | 4 | 4 | 5 |
| 59 | 16 | 1 | 5 | 4 | 1 | 3 | 4 | 3 | 5 | 3 |
| 60 | 16 | 0 | 4 | 4 | 2 | 3 | — | 4 | 4 | 5 |
| 61 | 16 | 0 | 4 | 4 | 4 | 3 | 4 | 3 | 3 | 4 |
| 62 | 16 | 1 | 5 | 4 | 4 | 4 | — | 5 | 4 | 4 |
| 62a | 16 | 0 | 3 | 4 | 3 | 3 | 3 | 3 | 3 | 4 |
| 62b | 16 | 0 | 4 | 4 | 3 | 4 | 3 | 3 | 3 | 4 |
| 63 | 16 | 1 | 4 | 4 | 4 | 3 | 1 | 3 | 2 | 4 |
| 64 | 16 | 1 | 5 | 5 | 5 | 5 | 5 | 5 | 5 | 5 |
| | 8 | 0 | 5 | 5 | 5 | 4 | 5 | 4 | 5 | 5 |
| 65 | 16 | 0 | 4 | 5 | 5 | 5 | 4 | 4 | 4 | 5 |
| 66 | 16 | 0 | 4 | 5 | 5 | 5 | 5 | 5 | 4 | 5 |
| 67 | 16 | 0 | 4 | 5 | 5 | 4 | 4 | 4 | 4 | 5 |
| | 8 | 0 | 4 | 4 | 3 | 4 | 3 | 3 | 3 | 5 |
| 68 | 16 | 1 | 5 | 5 | 5 | 5 | 4 | 5 | 5 | 5 |
| | 8 | 0 | 5 | 5 | 5 | 4 | 4 | 3 | 4 | 5 |
| 69 | 16 | 0 | 4 | 5 | 5 | 5 | 4 | 4 | 3 | 5 |
| 70 | 16 | 0 | 3 | 4 | 4 | 4 | 3 | 3 | 3 | 5 |
| 71 | 16 | 0 | 2 | 3 | 2 | 3 | 1 | 2 | 1 | 4 |
| 72 | 16 | 0 | 4 | 5 | 4 | 5 | 4 | 3 | 3 | 5 |
| 73 | 16 | 0 | 3 | 3 | 3 | 3 | 1 | 2 | 1 | 4 |
| 74 | 16 | 0 | 4 | 5 | 5 | 5 | 3 | 3 | 4 | 5 |
| 75 | 16 | 0 | 3 | 4 | 4 | 4 | 2 | 3 | 3 | 5 |
| 76 | 16 | 0 | 4 | 4 | 4 | 4 | 3 | 3 | 3 | 5 |
| 77 | 16 | 0 | 4 | 4 | 3 | 2 | 4 | 2 | 3 | 4 |
| 78 | 16 | 0 | 3 | 4 | 4 | 4 | 5 | 2 | 3 | 5 |
| 79 | 16 | 0 | 5 | 5 | 5 | 4 | 3 | 4 | 4 | 5 |
| 80 | 16 | 0 | 3 | 4 | 2 | 5 | 1 | 1 | 2 | 4 |
| 82 | 16 | 0 | 3 | 3 | 2 | 2 | 3 | 1 | 2 | 4 |
| 83 | 16 | 0 | 3 | 4 | 4 | 4 | 3 | 3 | 4 | 5 |
| 85 | 16 | 1 | 5 | 5 | 5 | 4 | 3 | 3 | 4 | 5 |
| 89 | 16 | 0 | 4 | 4 | 3 | 4 | 3 | 2 | 3 | 5 |

TABLE 4-continued

|  |  |  | Broadleaf Weeds | | | | Narrowleaf Weeds | | | |
| --- | --- | --- | --- | --- | --- | --- | --- | --- | --- | --- |
| Comd. No. | Dose (g/ha) | Cotton | Cal | Sol | Abu | Aes | Dig | Sat | Ech | Sor |
| 94 | 16 | 0 | 4 | 5 | 5 | 5 | 4 | 3 | 4 | 5 |
| 101 | 16 | 0 | 4 | 5 | 4 | 4 | 4 | 3 | 5 | 5 |
| 104 | 16 | 0 | 4 | 5 | 4 | 4 | 4 | 3 | 4 | 5 |
| 106 | 16 | 0 | 4 | 5 | 3 | 3 | 4 | 3 | 4 | 5 |
| 107 | 16 | 0 | 5 | 5 | 4 | 5 | 5 | 5 | 5 | 5 |
| 108 | 16 | 0 | 5 | 5 | 5 | 5 | 4 | 4 | 4 | 5 |
| 109 | 16 | 0 | 5 | 5 | 5 | 5 | 3 | 3 | 3 | 5 |
| 110 | 16 | 0 | 4 | 5 | 5 | 4 | 4 | 4 | 4 | 5 |
|  | 8 | 0 | 4 | 4 | 3 | 4 | 3 | 3 | 3 | 5 |
| 111 | 16 | 1 | 5 | 5 | 5 | 5 | 4 | 5 | 5 | 5 |
|  | 8 | 0 | 5 | 5 | 4 | 4 | 4 | 3 | 4 | 5 |
| 112 | 16 | 0 | 4 | 5 | 3 | 3 | 4 | 4 | 3 | 5 |
| 113 | 16 | 0 | 3 | 4 | 3 | 4 | 3 | 3 | 3 | 5 |
| 114 | 16 | 0 | 3 | 4 | 3 | 3 | 4 | 3 | 4 | 5 |
| 115 | 16 | 0 | 3 | 4 | 2 | 3 | 2 | 3 | 3 | 5 |
| 116 | 16 | 0 | 3 | 3 | 3 | 3 | 1 | 2 | 1 | 4 |
| 117 | 16 | 0 | 3 | 3 | 3 | 3 | 3 | 3 | 2 | 5 |
| 118 | 16 | 0 | 3 | 4 | 3 | 4 | 3 | 3 | 3 | 5 |
| 119 | 16 | 0 | 4 | 4 | 4 | 4 | 3 | 3 | 3 | 5 |
| 120 | 16 | 0 | 4 | 4 | 3 | 4 | 4 | 2 | 3 | 4 |
| 121 | 16 | 0 | 3 | 4 | 4 | 4 | 3 | 4 | 3 | 5 |
| 122 | 16 | 0 | 5 | 5 | 5 | 4 | 3 | 4 | 4 | 5 |
| 124 | 16 | 0 | 5 | 5 | 5 | 5 | 5 | 5 | 5 | 5 |
| 125 | 16 | 0 | 5 | 5 | 5 | 5 | 5 | 5 | 5 | 5 |
| 126 | 16 | 0 | 5 | 4 | 5 | 4 | 4 | 5 | 5 | 5 |
| 127 | 16 | 1 | 5 | 5 | 5 | 5 | 5 | 5 | 5 | 5 |
| 128 | 16 | 0 | 5 | 5 | 5 | 5 | 5 | 5 | 5 | 5 |
| 129 | 16 | 1 | 5 | 5 | 5 | 5 | 5 | 5 | 5 | 5 |
| 130 | 16 | 1 | 5 | 5 | 5 | 5 | 5 | 5 | 5 | 5 |
| 131 | 16 | 0 | 4 | 5 | 4 | 4 | 3 | 3 | 4 | 5 |
| 132 | 16 | 0 | 4 | 5 | 5 | 5 | 3 | 5 | 5 | 5 |
| 133 | 16 | 0 | 5 | 5 | 5 | 5 | 4 | 5 | 5 | 5 |
| 134 | 16 | 0 | 4 | 5 | 5 | 5 | 3 | 5 | 4 | 5 |
| 136 | 16 | 0 | 5 | 5 | 5 | 5 | 3 | 4 | 5 | 5 |
| 137 | 16 | 0 | 5 | 5 | 5 | 5 | 5 | 5 | 5 | 5 |
| 141 | 16 | 1 | 5 | 5 | 4 | 5 | 3 | 5 | 4 | 5 |
| 142 | 8 | 0 | 5 | 5 | 5 | 5 | 4 | 5 | 5 | 3 |
|  | 16 | 1 | 5 | 5 | 5 | 5 | 5 | 5 | 5 | 5 |
| 143 | 16 | 0 | 4 | 5 | 4 | 5 | 5 | 5 | 4 | 5 |
| 144 | 16 | 0 | 4 | 5 | 5 | 4 | 4 | 4 | 4 | 5 |
| 145 | 16 | 1 | 5 | 5 | 5 | 5 | 4 | 3 | 5 | 3 |
| 146 | 16 | 0 | 5 | 5 | 4 | 5 | 5 | 4 | 3 | 5 |
| 147 | 16 | 1 | 5 | 5 | 5 | 5 | 5 | 5 | 5 | 5 |
| 148 | 16 | 0 | 5 | 5 | 5 | 5 | 5 | 5 | 3 | 5 |
| 149 | 16 | 0 | 4 | 4 | 3 | 4 | 4 | 3 | 3 | 5 |
| 150 | 16 | 0 | 5 | 5 | 5 | 4 | 5 | 5 | 3 | 5 |
| 151 | 16 | 0 | 5 | 5 | 3 | 5 | 4 | 4 | 4 | 5 |
| 152 | 16 | 0 | 5 | 5 | 5 | 5 | 4 | 4 | 4 | 5 |
| 153 | 16 | 0 | 5 | 5 | 2 | 5 | 4 | 3 | 4 | 5 |
| 154 | 16 | 0 | 3 | 3 | 2 | 3 | 1 | 2 | 2 | 4 |
| 155 | 16 | 1 | 5 | 5 | 5 | 5 | 5 | 5 | 5 | 5 |
|  | 8 | 0 | 5 | 5 | 5 | 5 | 5 | 5 | 5 | 5 |
| 156 | 16 | 0 | 5 | 5 | 5 | 5 | 4 | 5 | 5 | 5 |
| 157 | 16 | 1 | 5 | 5 | 4 | 5 | 5 | 4 | 4 | 5 |
| 158 | 16 | 0 | 4 | 5 | 2 | 3 | 1 | 2 | 2 | 4 |
| 159 | 16 | 0 | 5 | 5 | 5 | 5 | 3 | 4 | 3 | 5 |
| 160 | 16 | 1 | 5 | 5 | 5 | 5 | 5 | 5 | 5 | 5 |
| 161 | 16 | 0 | 4 | 5 | 4 | 5 | 5 | 3 | 3 | 5 |
| 162 | 16 | 0 | 4 | 4 | 4 | 4 | 2 | 3 | 3 | 5 |
| 163 | 16 | 0 | 5 | 5 | 2 | 4 | 3 | 3 | 2 | 5 |
| 164 | 16 | 1 | 5 | 5 | 5 | 5 | 2 | 5 | 5 | 3 |
| 165 | 16 | 0 | 5 | 5 | 5 | 5 | 5 | 5 | 5 | 5 |
| 166 | 16 | 0 | 2 | 2 | 0 | 2 | 3 | 1 | 1 | 4 |
| 167 | 16 | 0 | 2 | 3 | 0 | 2 | 2 | 1 | 1 | 4 |
| 170 | 16 | 0 | 5 | 5 | 5 | 5 | 5 | 5 | 5 | 5 |
| 171 | 16 | 0 | 3 | 3 | 2 | 2 | 2 | 1 | 3 | 4 |
| 172 | 16 | 0 | 5 | 5 | 4 | 4 | 5 | 3 | 5 | 5 |
| 173 | 16 | 0 | 5 | 5 | 3 | 4 | 5 | 2 | 4 | 5 |
| 174 | 16 | 1 | 5 | 5 | 5 | 5 | 5 | 5 | 5 | 5 |
| 175 | 16 | 0 | 4 | 5 | 5 | 5 | 4 | 4 | 4 | 5 |
| 176 | 16 | 0 | 5 | 5 | 5 | 5 | 5 | 5 | 5 | 5 |
| 177 | 16 | 0 | 5 | 5 | 5 | 4 | 4 | 5 | 5 | 5 |
| 178 | 16 | 1 | 5 | 5 | 5 | 5 | 5 | 5 | 5 | 5 |
| 179 | 16 | 0 | 4 | 5 | 5 | 5 | 4 | 4 | 3 | 5 |
| 180 | 16 | 0 | 5 | 5 | 5 | 5 | 5 | 5 | 5 | 5 |

TABLE 4-continued

| Comd. No. | Dose (g/ha) | Cotton | Broadleaf Weeds | | | | Narrowleaf Weeds | | | |
|---|---|---|---|---|---|---|---|---|---|---|
| | | | Cal | Sol | Abu | Aes | Dig | Sat | Ech | Sor |
| | 8 | 0 | 5 | 5 | 5 | 5 | 5 | 5 | 5 | 5 |
| 181 | 16 | 0 | 4 | 5 | 5 | 5 | 5 | 5 | 3 | 5 |
| 182 | 16 | 0 | 5 | 5 | 5 | 5 | 5 | 5 | 5 | 5 |
| 183 | 16 | 0 | 4 | 5 | 5 | 5 | 3 | 4 | 4 | 5 |
| 184 | 16 | 0 | 4 | 4 | 5 | 5 | 2 | 4 | 4 | 5 |
| 185 | 16 | 0 | 5 | 5 | 5 | 5 | 5 | 5 | 5 | 5 |
| 186 | 16 | 1 | 5 | 5 | 5 | 5 | 4 | 4 | 4 | 5 |
| 187 | 16 | 1 | 5 | 5 | 5 | 5 | 5 | 5 | 4 | 5 |
| 188 | 16 | 0 | 4 | 5 | 5 | 5 | 4 | 4 | 3 | — |
| 189 | 16 | 1 | 5 | 5 | 5 | 5 | 4 | 4 | 4 | 5 |
| 190 | 16 | 1 | 5 | 5 | 5 | 5 | 4 | 4 | 4 | — |
| 191 | 16 | 1 | 5 | 5 | 5 | 5 | 4 | 4 | 4 | 4 |
| 192 | 16 | 1 | 5 | 5 | 5 | 5 | 5 | 5 | 4 | 4 |
| 193 | 16 | 0 | 5 | 5 | 5 | 5 | 5 | 4 | 5 | 5 |
| 194 | 16 | 0 | 5 | 5 | 5 | 5 | 4 | 4 | 4 | 5 |
| 195 | 16 | 0 | 5 | 4 | 5 | 5 | 4 | 4 | 3 | 5 |
| 196 | 16 | 0 | 5 | 5 | 5 | 5 | 4 | 4 | 3 | 4 |
| 197 | 8 | 0 | 5 | 5 | 5 | 5 | 5 | 5 | — | 5 |
| 198 | 16 | 0 | 5 | 4 | 5 | 5 | 5 | 4 | — | 5 |
| 199 | 16 | 0 | 5 | 4 | 5 | 5 | 5 | 4 | — | 5 |
| 200 | 16 | 0 | 5 | 4 | 5 | 5 | 5 | 4 | — | 5 |
| 201 | 8 | 0 | 5 | 4 | 5 | 5 | 5 | 5 | — | 5 |
| 202 | 16 | 0 | 5 | 4 | 5 | 5 | 5 | 5 | — | 5 |
| 203 | 16 | 0 | 5 | 4 | 5 | 5 | 5 | 4 | — | 5 |
| 204 | 16 | 0 | 5 | 4 | 5 | 5 | 5 | 5 | — | 5 |
| 205 | 16 | 1 | 5 | 5 | 5 | 5 | 5 | 5 | 3 | — |
| 206 | 16 | 0 | 5 | 5 | 5 | 5 | 5 | 5 | 5 | — |
| 207 | 16 | 1 | 5 | 5 | 5 | 5 | 5 | 5 | 4 | — |
| 208 | 16 | 0 | 5 | 5 | 3 | 3 | 4 | 4 | 5 | 4 |
| 209 | 16 | 0 | 1 | 1 | 1 | 1 | 0 | 0 | 0 | 0 |
| 210 | 16 | 0 | 5 | 5 | 5 | 4 | 4 | 3 | 3 | — |
| 211 | 16 | 0 | 5 | 5 | 5 | 4 | 3 | 3 | 3 | — |
| 212 | 16 | 0 | 5 | 5 | 5 | 4 | 3 | 4 | 3 | — |
| 213 | 16 | 0 | 5 | 5 | 4 | 4 | 5 | 5 | — | 5 |
| 214 | 16 | 0 | 5 | 5 | 4 | 4 | 5 | 4 | — | 5 |
| 215 | 16 | 0 | 5 | 5 | 5 | 3 | 5 | 5 | — | 5 |
| 216 | 8 | 0 | 5 | 5 | 4 | 4 | 5 | 5 | — | 5 |
| 217 | 16 | 0 | 5 | 3 | 4 | 4 | 3 | 4 | 5 | 4 |
| 218 | 16 | 0 | 4 | 2 | 4 | 3 | 1 | 1 | 0 | 0 |
| 219 | 16 | 0 | 5 | 5 | 4 | 3 | 5 | 4 | 5 | — |

TEST EXAMPLE 2

Foliage Treatment after the Emergence of Weeds in Upland

Test plants were sown in the same manner as described in Test Example 1, and cover with soil of a thickness of from 0.5 cm. The pot was cultured in a glass chamber at a temperature within a range 20° to 25° C. for 10 to 14 days. When each plant grew to the stage of 3–4 leaves, a predetermined amount (12 ml per each pot) of an emulsifiable concentrate prepared in accordance with Formulation Example 1 was evenly sprayed to the foliage. The evaluation was conducted on the 30th day after the treatment with the herbicide. The results were evaluated in accordance with the standards as identified in Table 3 and shown by the index numbers in Table 5.

TABLE 5

| Comd. No. | Dose (g/ha) | Cotton | Broadleaf Weeds | | | | Narrrowleaf Weeds | | | |
|---|---|---|---|---|---|---|---|---|---|---|
| | | | Cal | Sol | Abu | Aes | Dig | Sat | Ech | Sor |
| 2 | 16 | 1 | 5 | 5 | 4 | 5 | 2 | 2 | 3 | 4 |
| 8 | 16 | 1 | 5 | 4 | 3 | 5 | 4 | 3 | 3 | 4 |
| 29a | 16 | 0 | 5 | 5 | 5 | 5 | 2 | 3 | 3 | 4 |
| 29b | 16 | 0 | 4 | 4 | 4 | 4 | 2 | 4 | 3 | 4 |
| 31a | 16 | 0 | 5 | 5 | 5 | 5 | 1 | 2 | 4 | 5 |
| | 8 | 0 | 5 | 2 | 5 | 5 | 1 | 2 | 4 | 5 |
| 31b | 16 | 0 | 4 | 4 | 3 | 2 | 2 | 3 | 3 | 4 |
| 34 | 16 | 0 | 4 | 4 | 5 | 5 | 0 | 3 | 4 | 5 |
| | 8 | 0 | 4 | 4 | 5 | 5 | 0 | 2 | 2 | 4 |
| 35 | 16 | 0 | 5 | 4 | 5 | 5 | 2 | 5 | 5 | 5 |
| | 8 | 0 | 5 | 4 | 5 | 5 | 1 | 3 | 3 | 5 |
| 36 | 16 | 0 | 5 | 5 | 5 | 5 | 2 | 5 | 5 | 5 |
| | 8 | 0 | 5 | 2 | 5 | 5 | — | 1 | 1 | 5 |
| 37 | 16 | 0 | 5 | 5 | 5 | 4 | 4 | 4 | 4 | 5 |

TABLE 5-continued

| | | | Broadleaf Weeds | | | | Narrrowleaf Weeds | | | |
|---|---|---|---|---|---|---|---|---|---|---|
| Comd. No. | Dose (g/ha) | Cotton | Cal | Sol | Abu | Aes | Dig | Sat | Ech | Sor |
| | 8 | 0 | 5 | 4 | 4 | 4 | 3 | 3 | 4 | 5 |
| 39 | 16 | 0 | 5 | 5 | 5 | 5 | 0 | 4 | 4 | 5 |
| | 8 | 0 | 4 | 4 | 4 | 4 | 0 | 3 | 3 | 5 |
| 41 | 16 | 0 | 5 | 4 | 4 | 4 | 0 | 3 | 3 | 5 |
| 43a | 16 | 0 | 5 | 4 | 5 | 4 | 1 | 3 | 3 | 4 |
| 43b | 16 | 0 | 4 | 4 | 4 | 4 | 1 | 3 | 4 | 4 |
| 45 | 16 | 0 | 5 | 5 | 5 | 5 | 2 | 5 | 5 | 5 |
| | 8 | 0 | 5 | 5 | 5 | 5 | 2 | 5 | 5 | 5 |
| 46a | 16 | 0 | 4 | 4 | 2 | 4 | 2 | 4 | 3 | 2 |
| 46b | 16 | 0 | 4 | 3 | 3 | 4 | 2 | 3 | 3 | 2 |
| 48a | 16 | — | 5 | 5 | 3 | 3 | 3 | 5 | 3 | 2 |
| 48b | 16 | 3 | 4 | 5 | 3 | 3 | 4 | 4 | 3 | 2 |
| 57a | 16 | — | 5 | 5 | 3 | 3 | 4 | 4 | 3 | 2 |
| 57b | 16 | — | 5 | 5 | 3 | 3 | 4 | 5 | 2 | 2 |
| 58 | 16 | 0 | 5 | 4 | 5 | 5 | 2 | 4 | 5 | 5 |
| 60 | 8 | 0 | 5 | 4 | 5 | 5 | 2 | 4 | 5 | 5 |
| | 4 | 0 | 5 | 4 | 5 | 5 | 0 | 1 | 3 | 4 |
| 61 | 16 | 0 | 5 | 5 | 5 | 4 | 3 | 4 | 3 | 5 |
| 62a | 8 | 0 | 4 | 4 | 2 | 3 | 1 | 2 | 2 | 3 |
| 62b | 16 | 0 | 4 | 4 | 4 | 4 | 3 | 4 | 3 | 4 |
| 63 | 16 | 1 | 5 | 5 | 5 | 5 | — | — | 5 | 5 |
| | 8 | 0 | 5 | 2 | 5 | 5 | 1 | 1 | 5 | — |
| 64 | 16 | 1 | 2 | 1 | 4 | 4 | 0 | 2 | 2 | 4 |
| 65 | 16 | 1 | 5 | 5 | 5 | 5 | 3 | 3 | 4 | 5 |
| | 8 | 0 | 4 | 5 | 5 | 5 | 3 | 3 | 3 | 5 |
| 66 | 16 | 1 | 5 | 5 | 5 | 5 | 3 | 5 | 5 | 5 |
| | 8 | 0 | 4 | 5 | 5 | 5 | 3 | 3 | 3 | 5 |
| 67 | 16 | 0 | 5 | 5 | 5 | 5 | 2 | 2 | 2 | 5 |
| | 8 | 0 | 5 | 5 | 5 | 5 | 2 | 2 | 2 | 5 |
| 68 | 8 | 0 | 5 | 5 | 5 | 5 | 5 | 4 | 5 | 5 |
| | 4 | 0 | 4 | 5 | 5 | 5 | 5 | 4 | 5 | 5 |
| 69 | 8 | 0 | 5 | 5 | 5 | 5 | 1 | 4 | 4 | 5 |
| 70 | 16 | 0 | 4 | 5 | 5 | 4 | 2 | 2 | 3 | 5 |
| 71 | 16 | 0 | 4 | 5 | 5 | 4 | 3 | 2 | 4 | 5 |
| 72 | 16 | 0 | 5 | 5 | 5 | 5 | 2 | 3 | 5 | 5 |
| 73 | 16 | 0 | 4 | 5 | 4 | 5 | 3 | 3 | 4 | 5 |
| 74 | 16 | 0 | 5 | 5 | 5 | 5 | 4 | 3 | 3 | 5 |
| 75 | 16 | 0 | 5 | 5 | 5 | 5 | 3 | 3 | 4 | 5 |
| 76 | 16 | 0 | 5 | 5 | 5 | 5 | 4 | 4 | 5 | 5 |
| | 8 | 0 | 5 | 5 | 5 | 5 | 3 | 3 | 5 | 5 |
| 77 | 16 | 1 | 4 | 4 | 5 | 5 | 2 | 3 | 5 | 5 |
| | 8 | 0 | 4 | 4 | 4 | 5 | 1 | 2 | 4 | 5 |
| 78 | 16 | 0 | 5 | 4 | 5 | 4 | 2 | 3 | 5 | 5 |
| 79 | 16 | 0 | 4 | 5 | 5 | 5 | 3 | 4 | 4 | 5 |
| 80 | 16 | 0 | 5 | 5 | 5 | 5 | 4 | 4 | 5 | 5 |
| | 8 | 0 | 5 | 5 | 5 | 5 | 3 | 3 | 5 | 5 |
| 81 | 16 | 0 | 4 | 5 | 4 | 5 | 3 | 2 | 3 | 5 |
| 82 | 16 | 0 | 4 | 4 | 4 | 3 | 3 | 3 | 4 | 4 |
| 83 | 16 | 0 | 4 | 4 | 5 | 5 | 4 | 3 | 3 | 5 |
| 84 | 16 | 0 | 5 | 5 | 5 | 4 | 3 | 3 | 5 | 5 |
| 85 | 16 | 1 | 5 | 5 | 5 | 4 | 4 | 4 | 4 | 5 |
| 86 | 16 | 0 | 5 | 5 | 5 | 5 | 2 | 4 | 4 | 5 |
| 87 | 16 | 1 | 5 | 5 | 5 | 5 | 4 | 3 | 5 | 5 |
| | 8 | 0 | 4 | 5 | 5 | 4 | 2 | 2 | 4 | 4 |
| 88 | 16 | 0 | 4 | 4 | 5 | 4 | 2 | 2 | 3 | 5 |
| 89 | 16 | 0 | 4 | 5 | 5 | 5 | 3 | 3 | 5 | 5 |
| 90 | 16 | 0 | 4 | 5 | 3 | 3 | 2 | 2 | 4 | 5 |
| 91 | 16 | 0 | 4 | 5 | 4 | 4 | 2 | 2 | 4 | 5 |
| 92 | 16 | 0 | 4 | 5 | 4 | 4 | 2 | 2 | 4 | 5 |
| 93 | 16 | 0 | 4 | 5 | 4 | 4 | 3 | 2 | 3 | 4 |
| 94 | 16 | 0 | 4 | 5 | 5 | 5 | 3 | 2 | 3 | 4 |
| 95 | 16 | 0 | 4 | 5 | 4 | 5 | 3 | 3 | 4 | 5 |
| 96 | 16 | 0 | 4 | 5 | 5 | 4 | 3 | 2 | 4 | 4 |
| 97 | 16 | 0 | 3 | 4 | 4 | 4 | 3 | 3 | 3 | 4 |
| 98 | 16 | 0 | 3 | 5 | 4 | 4 | 2 | 2 | 4 | 5 |
| 99 | 16 | 0 | 4 | 4 | 5 | 4 | 2 | 2 | 4 | 4 |
| 100 | 16 | 0 | 2 | 3 | 3 | 3 | 2 | 2 | 3 | 3 |
| 101 | 16 | 0 | 4 | 5 | 5 | 4 | 2 | 3 | 4 | 5 |
| 102 | 16 | 0 | 4 | 5 | 4 | 4 | 3 | 3 | 5 | 5 |
| 103 | 16 | 0 | 3 | 4 | 3 | 3 | 2 | 2 | 3 | 4 |
| 104 | 16 | 0 | 4 | 4 | 5 | 5 | 4 | 3 | 5 | 5 |
| 105 | 16 | 0 | 4 | 5 | 4 | 3 | 4 | 3 | 3 | 5 |
| 106 | 16 | 0 | 3 | 3 | 3 | 3 | 2 | 2 | 3 | 4 |
| 107 | 16 | 0 | 5 | 5 | 5 | 5 | 2 | 4 | 5 | 5 |
| 108 | 16 | 0 | 5 | 5 | 5 | 5 | 3 | 4 | 5 | 5 |

TABLE 5-continued

|  |  |  | Broadleaf Weeds | | | | Narrowleaf Weeds | | | |
| --- | --- | --- | --- | --- | --- | --- | --- | --- | --- | --- |
| Comd. No. | Dose (g/ha) | Cotton | Cal | Sol | Abu | Aes | Dig | Sat | Ech | Sor |
| 109 | 16 | 0 | 5 | 5 | 5 | 5 | 2 | 4 | 5 | 5 |
| 110 | 16 | 0 | 5 | 5 | 5 | 5 | 2 | 4 | 5 | 5 |
| 111 | 16 | 0 | 5 | 5 | 5 | 5 | 3 | 4 | 5 | 5 |
| 112 | 16 | 0 | 5 | 5 | 5 | 5 | 3 | 4 | 5 | 5 |
| 113 | 16 | 0 | 5 | 5 | 5 | 4 | 3 | 4 | 5 | 5 |
| 114 | 16 | 0 | 5 | 5 | 5 | 5 | 5 | 5 | 5 | 5 |
| 115 | 16 | 0 | 5 | 5 | 5 | 5 | 2 | 5 | 5 | 5 |
| 116 | 16 | 0 | 5 | 5 | 4 | 5 | 3 | 5 | 5 | 5 |
| 117 | 16 | 0 | 5 | 5 | 5 | 5 | 1 | 5 | 5 | 5 |
| 118 | 16 | 0 | 5 | 5 | 5 | 5 | 2 | 5 | 5 | 5 |
| 119 | 16 | 0 | 5 | 5 | 5 | 5 | 4 | 4 | 5 | 5 |
| 120 | 16 | 1 | 5 | 5 | 5 | 5 | 4 | 4 | 5 | 5 |
| 121 | 16 | 0 | 5 | 4 | 5 | 4 | 2 | 3 | 5 | 5 |
| 122 | 16 | 0 | 4 | 5 | 5 | 5 | 3 | 4 | 4 | 5 |
| 124 | 16 | 0 | 5 | 5 | 5 | 5 | 4 | 5 | 5 | 5 |
| 125 | 16 | 1 | 5 | 5 | 5 | 5 | 5 | 5 | 5 | 5 |
| 126 | 16 | 0 | 5 | 5 | 5 | 5 | 4 | 5 | 5 | 5 |
| 127 | 16 | 1 | 5 | 5 | 5 | 5 | 3 | 5 | 5 | 5 |
| 128 | 16 | 1 | 5 | 5 | 5 | 5 | 3 | 5 | 5 | 5 |
| 129 | 16 | 0 | 5 | 5 | 5 | 5 | 3 | 4 | 4 | 5 |
| 130 | 16 | 1 | 5 | 5 | 5 | 5 | 4 | 5 | 5 | 5 |
| 131 | 16 | 1 | 5 | 5 | 5 | 5 | 4 | 5 | 5 | 5 |
| 132 | 16 | 0 | 4 | 5 | 5 | 5 | 3 | 5 | 5 | 5 |
| 133 | 16 | 0 | 4 | 5 | 3 | 4 | 2 | 2 | 4 | 5 |
| 134 | 16 | 0 | 5 | 5 | 4 | 5 | 2 | 5 | 4 | 5 |
| 135 | 16 | 0 | 4 | 5 | 4 | 4 | 2 | 2 | 4 | 5 |
| 136 | 16 | 0 | 4 | 5 | 4 | 4 | 2 | 2 | 3 | 4 |
| 137 | 16 | 0 | 4 | 5 | 4 | 5 | 2 | 3 | 3 | 5 |
| 138 | 16 | 0 | 5 | 5 | 5 | 5 | 3 | 5 | 5 | 5 |
| 139 | 16 | 0 | 5 | 5 | 5 | 4 | 4 | 5 | 5 | 5 |
| 140 | 16 | 0 | 5 | 4 | 4 | 5 | 3 | 5 | 4 | 5 |
| 141 | 16 | 0 | 5 | 5 | 5 | 5 | 3 | 4 | 4 | 5 |
| 142 | 16 | 0 | 5 | 5 | 5 | 5 | 3 | 5 | 5 | 5 |
|  | 16 | 0 | 5 | 5 | 5 | 5 | 3 | 5 | 5 | 5 |
| 143 | 16 | 0 | 5 | 5 | 5 | 5 | 3 | 5 | 5 | 5 |
| 144 | 16 | 0 | 5 | 5 | 5 | 5 | 3 | 4 | 4 | 5 |
| 145 | 16 | 0 | 5 | 5 | 5 | 5 | 4 | 4 | 4 | 5 |
| 146 | 16 | 0 | 5 | 5 | 5 | 5 | 4 | 4 | 4 | 5 |
| 147 | 16 | 0 | 3 | 5 | 5 | 5 | 4 | 5 | 5 | 5 |
| 148 | 16 | 0 | 4 | 5 | 5 | 4 | 3 | 3 | 5 | 5 |
| 149 | 16 | 0 | 3 | 3 | 2 | 3 | 2 | 3 | 4 | 5 |
| 150 | 16 | 0 | 4 | 5 | 5 | 5 | 3 | 4 | 5 | 5 |
| 151 | 16 | 0 | 4 | 4 | 2 | 4 | 1 | 2 | 2 | 4 |
| 152 | 16 | 0 | 5 | 5 | 5 | 5 | 5 | 5 | 5 | 5 |
| 153 | 16 | 0 | 5 | 5 | 5 | 5 | 5 | 5 | 5 | 5 |
| 154 | 16 | 0 | 5 | 5 | 5 | 5 | 2 | 4 | 4 | 5 |
| 155 | 16 | 0 | 4 | 5 | 3 | 4 | 0 | 3 | 3 | 5 |
| 156 | 16 | 0 | 5 | 5 | 3 | 5 | 2 | 3 | 3 | 5 |
| 157 | 16 | 0 | 5 | 5 | 4 | 4 | 3 | 3 | 5 | 5 |
| 158 | 16 | 0 | 5 | 5 | 5 | 5 | 5 | 5 | 5 | 5 |
| 159 | 16 | 0 | 5 | 5 | 5 | 5 | 3 | 4 | 4 | 5 |
| 160 | 16 | 1 | 5 | 5 | 5 | 5 | 4 | 5 | 5 | 5 |
| 161 | 16 | 0 | 5 | 5 | 5 | 5 | 2 | 4 | 5 | 5 |
| 162 | 16 | 0 | 5 | 5 | 5 | 5 | 3 | 4 | 5 | 5 |
| 163 | 16 | 0 | 5 | 5 | 5 | 5 | 4 | 4 | 5 | 5 |
| 164 | 16 | 0 | 5 | 5 | 5 | 5 | 1 | 5 | 5 | 5 |
| 165 | 16 | 0 | 5 | 5 | 5 | 5 | 5 | 5 | 5 | 5 |
| 166 | 16 | 0 | 5 | 5 | 5 | 5 | 3 | 4 | 5 | 5 |
| 167 | 16 | 0 | 5 | 5 | 5 | 5 | 3 | 4 | 5 | 5 |
| 168 | 16 | 0 | 4 | 4 | 4 | 5 | 3 | 2 | 3 | 5 |
| 169 | 16 | 0 | 5 | 5 | 4 | 5 | 3 | 3 | 4 | 5 |
| 170 | 16 | 0 | 5 | 5 | 5 | 5 | 3 | 5 | 5 | 5 |
| 172 | 16 | 0 | 5 | 5 | 3 | 5 | 3 | 3 | 3 | 5 |
| 173 | 16 | 0 | 5 | 5 | 3 | 4 | 3 | 3 | 3 | 5 |
| 174 | 16 | 0 | 4 | 4 | 5 | 4 | 3 | 4 | 3 | 5 |
| 175 | 16 | 0 | 5 | 5 | 5 | 5 | 3 | 3 | 4 | 5 |
| 176 | 16 | 0 | 5 | 5 | 5 | 5 | 3 | 5 | 5 | 5 |
| 177 | 16 | 0 | 5 | 5 | 5 | 5 | 2 | 5 | 4 | 5 |
| 178 | 16 | 0 | 5 | 5 | 5 | 5 | 5 | 4 | 5 | 5 |
| 179 | 16 | 0 | 5 | 5 | 5 | 5 | 3 | 4 | 4 | 5 |
| 180 | 16 | 0 | 5 | 5 | 5 | 5 | 5 | 5 | 5 | 5 |
| 181 | 16 | 0 | 5 | 5 | 5 | 4 | 3 | 5 | 5 | 5 |
| 182 | 16 | 0 | 5 | 5 | 5 | 5 | 3 | 3 | 5 | 5 |
| 183 | 16 | 0 | 5 | 5 | 5 | 5 | 3 | 3 | 5 | 5 |
| 184 | 16 | 0 | 5 | 5 | 5 | 5 | 4 | 5 | 5 | 5 |

TABLE 5-continued

| Comd. No. | Dose (g/ha) | Cotton | Broadleaf Weeds | | | | Narrowleaf Weeds | | | |
|---|---|---|---|---|---|---|---|---|---|---|
| | | | Cal | Sol | Abu | Aes | Dig | Sat | Ech | Sor |
| 185 | 16 | 1 | 5 | 5 | 5 | 5 | 5 | 5 | 5 | 5 |
| 186 | 16 | 0 | 5 | 5 | 5 | 5 | 3 | 4 | 5 | 3 |
| 187 | 16 | 0 | 5 | 5 | 5 | 5 | 4 | 3 | 2 | 4 |
| 188 | 16 | 0 | 5 | 5 | 5 | 5 | 4 | 5 | 3 | — |
| 189 | 16 | 1 | 5 | 5 | 5 | 5 | 3 | 4 | 4 | 2 |
| 190 | 16 | 1 | 5 | 5 | 5 | 5 | 3 | 3 | 3 | — |
| 191 | 16 | 0 | 5 | 5 | 5 | 4 | 3 | 4 | 4 | 3 |
| 192 | 16 | 0 | 5 | 5 | 5 | 5 | 3 | 3 | 2 | 4 |
| 193 | 16 | 1 | 5 | 5 | 5 | 5 | 4 | 3 | 3 | 3 |
| 194 | 16 | 0 | 5 | 4 | 5 | 5 | 2 | 3 | 4 | 2 |
| 195 | 16 | 0 | 5 | 5 | 5 | 5 | 3 | 4 | 4 | 3 |
| 196 | 16 | 0 | 5 | 4 | 5 | 5 | 2 | 3 | 4 | 1 |
| 197 | 16 | 0 | 5 | 5 | 5 | 5 | 5 | 4 | — | 5 |
| 198 | 16 | 0 | 5 | 5 | 5 | 5 | 5 | 4 | — | 5 |
| 199 | 16 | 0 | 5 | 4 | 5 | 5 | 5 | 4 | — | 5 |
| 200 | 16 | 0 | 5 | 5 | 5 | 5 | 5 | 4 | — | 5 |
| 201 | 16 | 0 | 5 | 5 | 5 | 5 | 5 | 4 | — | 5 |
| 202 | 16 | 0 | 5 | 5 | 5 | 5 | 5 | 4 | — | 5 |
| 203 | 16 | 0 | 5 | 5 | 5 | 5 | 5 | 4 | — | 5 |
| 204 | 16 | 0 | 5 | 4 | 5 | 5 | 5 | 4 | — | 5 |
| 205 | 16 | 0 | 5 | 5 | 5 | 5 | 4 | 5 | 4 | — |
| 206 | 16 | 0 | 5 | 5 | 5 | 5 | 3 | 5 | 2 | — |
| 207 | 16 | 0 | 5 | 5 | 5 | 5 | 3 | 4 | 3 | — |
| 208 | 16 | 0 | 5 | 4 | 4 | 4 | 2 | 2 | 2 | 3 |
| 210 | 16 | 0 | 5 | 5 | 5 | 4 | 3 | 4 | 4 | — |
| 211 | 16 | 0 | 5 | 5 | 5 | 4 | 4 | 4 | 4 | — |
| 212 | 16 | 0 | 5 | 5 | 5 | 4 | 4 | 5 | 4 | — |
| 213 | 16 | 0 | 5 | 5 | 5 | 4 | 5 | 4 | — | 5 |
| 214 | 16 | 0 | 5 | 5 | 5 | 4 | 5 | 3 | — | 5 |
| 215 | 16 | 0 | 5 | 5 | 4 | 4 | 5 | 4 | — | 5 |
| 216 | 8 | 0 | 5 | 5 | 4 | 4 | 5 | 4 | — | 5 |
| 217 | 16 | 0 | 4 | 3 | 4 | 4 | 1 | 2 | 3 | 2 |
| 219 | 16 | 0 | 5 | 5 | 5 | 3 | 3 | 4 | 2 | 5 |

TEST EXAMPLE 3

Soil Treatment Test Compared with Known Compounds

As comparative Compounds, 6-chloro-2-(4,6-dimethoxy-pyrimidin-2-yl)oxy benzoic acid method methyl ester (A) and its phenoxyethyl ester (B) in European Patent Publication No. 249,708 were prepared by using a known method, and evaluated their herbicidal effects and phytotoxicities to cotton in accordance with Test Example 1.

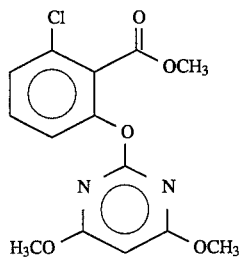
(A)

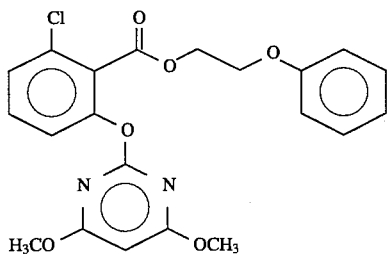
(B)

The results of the present test indicate, as shown in the following Table 6, that the compounds of the invention represented by the formula (I) exhibit superior herbicidal effects against weeds, moreover, can be used extremely safely for cotton.

TABLE 6

| Comd. No. | Dose (g/ha) | Cotton | Broadleaf Weeds | | | | Narrowleaf Weeds | | | |
|---|---|---|---|---|---|---|---|---|---|---|
| | | | Cal | Sol | Abu | Aes | Dig | Sat | Ech | Sor |
| 13 | 60 | | 5 | 5 | 5 | 5 | 5 | 5 | 5 | 5 |
| | 16 | | 5 | 5 | 5 | 5 | 5 | 5 | 5 | 5 |
| | 4 | | 5 | 5 | 4 | 4 | 5 | 5 | 5 | 5 |
| 16 | 60 | | 5 | 5 | 5 | 5 | 5 | 5 | 5 | 5 |
| | 16 | | 5 | 5 | 5 | 5 | 5 | 5 | 5 | 5 |

TABLE 6-continued

| Comd. No. | Dose (g/ha) | Cotton | Broadleaf Weeds | | | | Narrowleaf Weeds | | | |
|---|---|---|---|---|---|---|---|---|---|---|
| | | | Cal | Sol | Abu | Aes | Dig | Sat | Ech | Sor |
| | 4 | | 5 | 5 | 4 | 4 | 5 | 5 | 5 | 5 |
| 19 | 60 | | 5 | 5 | 5 | 5 | 5 | 5 | 5 | 5 |
| | 16 | | 5 | 4 | 5 | 5 | 5 | 5 | 2 | 5 |
| | 4 | | 5 | 4 | 4 | 3 | 3 | 2 | 1 | 4 |
| 23 | 60 | | 5 | 5 | 5 | 5 | 5 | 5 | 5 | 5 |
| | 16 | | 5 | 5 | 5 | 5 | 5 | 5 | 5 | 5 |
| | 4 | | 4 | 4 | 4 | 4 | 3 | 4 | 3 | 4 |
| 64 | 8 | 0 | 5 | 5 | 5 | 4 | 5 | 4 | 5 | 5 |
| | 4 | 0 | 4 | 5 | 5 | 3 | 4 | 4 | 4 | 5 |
| 68 | 16 | 1 | 5 | 5 | 5 | 4 | 4 | 5 | 5 | 5 |
| | 8 | 0 | 5 | 5 | 4 | 4 | 4 | 3 | 4 | 5 |
| 124 | 8 | 0 | 5 | 5 | 5 | 5 | 4 | 5 | 5 | 5 |
| | 4 | 0 | 5 | 5 | 5 | 5 | 3 | 5 | 5 | 5 |
| 130 | 16 | 1 | 5 | 5 | 5 | 5 | 4 | 5 | 5 | 5 |
| | 8 | 0 | 5 | 5 | 5 | 5 | 3 | 5 | 5 | 5 |
| 142 | 8 | 0 | 5 | 5 | 5 | 5 | 4 | 5 | 5 | 5 |
| | 4 | 0 | 5 | 5 | 4 | 4 | 4 | 4 | 4 | 5 |
| 147 | 16 | 1 | 5 | 5 | 5 | 5 | 5 | 5 | 5 | 5 |
| | 8 | 0 | 5 | 5 | 5 | 5 | 4 | 5 | 5 | 5 |
| 175 | 8 | 0 | 5 | 5 | 5 | 5 | 5 | 5 | 5 | 5 |
| | 4 | 0 | 5 | 5 | 3 | 5 | 3 | 4 | 2 | 4 |
| 170 | 8 | 0 | 5 | 5 | 5 | 5 | 5 | 5 | 5 | 5 |
| | 4 | 0 | 5 | 5 | 5 | 5 | 4 | 4 | 4 | 5 |
| 176 | 16 | 0 | 5 | 5 | 5 | 5 | 5 | 5 | 5 | 5 |
| | 8 | 0 | 5 | 5 | 3 | 5 | 5 | 4 | 5 | 5 |
| 180 | 16 | 0 | 5 | 5 | 5 | 5 | 5 | 5 | 5 | |
| | 8 | 0 | 5 | 5 | 5 | 5 | 5 | 5 | 5 | 5 |
| 193 | 16 | | 5 | 5 | 5 | 5 | 5 | 4 | 5 | 5 |
| 205 | 16 | | 5 | 5 | 5 | 5 | 5 | 5 | 3 | |
| 212 | 16 | | 5 | 5 | 5 | 4 | 3 | 4 | 3 | |
| A | 60 | | 3 | 4 | 3 | 5 | 1 | 0 | 1 | 1 |
| | 16 | | 2 | 3 | 0 | 3 | 0 | 0 | 0 | 0 |
| B | 60 | | 3 | 4 | 4 | 1 | 1 | 1 | 3 | 4 |
| | 16 | | 2 | 1 | 2 | 0 | 1 | 1 | 1 | 1 |

TEST EXAMPLE 4

Foliage Treatment Test Compared with Known Compounds

The test of herbicidal effects and phytotoxicities of the present compounds and above known compounds, carried out in the same manner as described in Test Example 2.

From the results of this test, it can be also expected that the compounds of the present invention have not only excellent herbicidal activities, but also satisfactory safety to cotton, as shown in the following Table 7.

TABLE 7

| Comd. No. | Dose (g/ha) | Cotton | Broadleaf Weeds | | | | Narrowleaf Weeds | | | |
|---|---|---|---|---|---|---|---|---|---|---|
| | | | Cal | Sol | Abu | Aes | Dig | Sat | Ech | Sor |
| 16 | 60 | | 5 | 5 | 5 | 5 | 5 | 5 | 5 | 5 |
| | 16 | | 5 | 5 | 5 | 5 | 5 | 5 | 5 | 5 |
| | 4 | | 3 | 5 | 5 | 4 | 3 | 5 | 5 | 5 |
| 35 | 60 | | 5 | 5 | 5 | 5 | 4 | 5 | 5 | 5 |
| | 16 | | 5 | 4 | 5 | 5 | 2 | 5 | 5 | 5 |
| | 4 | | 5 | 4 | 4 | 4 | 0 | 2 | 3 | 4 |
| 36 | 60 | | 5 | 5 | 5 | 5 | 4 | 5 | 5 | 5 |
| | 16 | | 5 | 2 | 5 | 5 | 2 | 5 | 5 | 5 |
| | 4 | | 1 | 0 | 5 | 5 | 0 | 1 | 1 | 5 |
| 45 | 60 | | 5 | 5 | 5 | 5 | 4 | 5 | 5 | 5 |
| | 16 | | 5 | 5 | 5 | 5 | 3 | 5 | 5 | 5 |
| | 4 | | 4 | 5 | 5 | 5 | 2 | 5 | 5 | 5 |
| 60 | 60 | | 5 | 5 | 5 | 5 | 4 | 5 | 5 | 5 |
| | 16 | | 5 | 4 | 5 | 5 | 2 | 4 | 5 | 5 |
| | 4 | | 5 | 4 | 5 | 5 | 0 | 1 | 3 | 4 |
| 66 | 8 | 0 | 5 | 5 | 5 | 5 | 2 | 3 | 4 | 5 |
| | 4 | 0 | 4 | 5 | 5 | 5 | 2 | 2 | 4 | 4 |
| 68 | 8 | 0 | 5 | 5 | 5 | 5 | 5 | 4 | 4 | 5 |
| | 4 | 0 | 4 | 5 | 5 | 5 | 5 | 4 | 5 | 5 |
| 76 | 16 | 0 | 5 | 5 | 5 | 5 | 4 | 4 | 5 | 5 |
| | 8 | 0 | 5 | 5 | 5 | 5 | 3 | 3 | 5 | 5 |

TABLE 7-continued

| Comd. No. | Dose (g/ha) | Cotton | Broadleaf Weeds | | | | Narrowleaf Weeds | | | |
|---|---|---|---|---|---|---|---|---|---|---|
| | | | Cal | Sol | Abu | Aes | Dig | Sat | Ech | Sor |
| 80 | 8 | 0 | 5 | 5 | 5 | 5 | 3 | 3 | 5 | 5 |
| | 4 | 0 | 4 | 5 | 5 | 5 | 2 | 3 | 4 | 5 |
| 124 | 8 | 0 | 5 | 5 | 5 | 5 | 2 | 5 | 5 | 5 |
| | 4 | 0 | 5 | 5 | 5 | 5 | 1 | 4 | 4 | 5 |
| 127 | 16 | 1 | 5 | 5 | 5 | 5 | 4 | 5 | 5 | 5 |
| | 8 | 0 | 5 | 5 | 5 | 5 | 3 | 3 | 5 | 5 |
| 142 | 8 | 0 | 5 | 5 | 5 | 5 | 3 | 5 | 5 | 5 |
| | 4 | 0 | 5 | 5 | 5 | 5 | 2 | 5 | 4 | 5 |
| 145 | 16 | 0 | 5 | 5 | 5 | 5 | 4 | 4 | 4 | 5 |
| | 8 | 0 | 4 | 5 | 5 | 5 | 3 | 4 | 3 | 5 |
| 158 | 16 | 0 | 5 | 5 | 5 | 5 | 5 | 5 | 5 | 5 |
| | 16 | 0 | 5 | 5 | 5 | 5 | 2 | 4 | 4 | 5 |
| 170 | 16 | 0 | 5 | 5 | 5 | 5 | 5 | 5 | 5 | 5 |
| | 4 | 0 | 5 | 5 | 5 | 5 | 2 | 4 | 5 | 5 |
| 176 | 16 | 0 | 5 | 5 | 5 | 5 | 3 | 5 | 5 | 5 |
| | 8 | 0 | 5 | 5 | 5 | 5 | 2 | 5 | 4 | 5 |
| 180 | 16 | 0 | 5 | 5 | 5 | 5 | 5 | 5 | 5 | 5 |
| | 8 | 0 | 5 | 5 | 5 | 5 | 4 | 5 | 5 | 5 |
| 195 | 16 | | 5 | 5 | 5 | 5 | 3 | 4 | 3 | 4 |
| 205 | 16 | | 5 | 5 | 5 | 5 | 4 | 5 | 4 | |
| 212 | 16 | | 5 | 5 | 5 | 4 | 4 | 5 | 4 | |
| A | 60 | | 5 | 3 | 2 | 5 | 0 | 0 | 2 | 2 |
| | 16 | | 2 | 2 | 1 | 5 | 0 | 0 | 0 | 0 |
| B | 60 | | 1 | 2 | 3 | 1 | 0 | 0 | 2 | 2 |
| | 16 | | 1 | 1 | 1 | 0 | 0 | 0 | 0 | 1 |

TEST EXAMPLE 5

Soil Treatment before the Emergence of Weeds in Paddy Field

Squarish pots (30×15×10 cm) were filled with the sterilized soil of paddy field (piedmont clay, pH 5.5–6.0), and, in a 450 cm² pot filled with soil, seeds of rice plant and 10 sorts of weeds were sown or planted, and covered with soil of a thickness of from 0.5 cm. For the soil treatment, a predetermined amount (12 ml per each pot) of an emulsifiable concentrate prepared in accordance with Formulation Example 1 was uniformly applied to the soil surface one day after the plantation. The pot was cultivated and observed for 4 weeks, and the evaluation was conducted on the last day of 4th week after the treatment with the herbicide. The results were evaluated in accordance with the standards as identified in Table 3 and shown by the index numbers in Table 8.

Note 2. The abbreviations of the tested plants are as follows (the same abbreviations are used in othertables).

| | |
|---|---|
| Ory: | rice plant (*Oryxa sativar*) |
| Ane: | *Aneileme keisak* |
| Esh.o: | *Echinochloa crus-galli* var. *oryzicola* |
| Sci: | *Scirpus jumcoides* |
| Mon: | monochoria (*Monochoria varinalis*) |
| Cyp: | flatsedge (*Cyperus difformis*) |
| Sag: | *Sagittaria pygmaea* |
| Sag.t: | *Sagittaria trifolia* |
| Ele: | *Eleocharis kuroquwai* |
| Pot: | *Potamogeton distinnctus* |

TABLE 8

| Comd. No. | Dose g/ha | Ory | Ane | Ech.o | Sci | Mon | Cyp | Sag | Sag.t | Ele | Pot |
|---|---|---|---|---|---|---|---|---|---|---|---|
| 2 | 0 | 4 | 1 | 4 | 4 | — | 4 | 3 | 4 | 4 | 4 |
| 9 | 1 | — | 2 | 4 | 4 | 4 | — | 4 | 5 | 4 | 4 |
| 29a | 1 | 3 | 4 | 4 | 4 | 4 | 5 | 4 | 5 | 4 | 5 |
| 36 | 1 | — | 2 | 4 | 4 | 3 | 4 | 0 | 4 | 4 | 4 |
| 37 | 0 | 4 | 2 | 3 | 3 | 1 | 4 | 4 | 4 | 4 | 4 |
| 42 | 1 | — | 3 | 4 | 4 | 3 | 4 | 4 | 3 | 4 | 4 |
| 47 | 1 | — | 3 | 4 | 4 | 3 | 4 | 4 | 3 | 4 | 4 |
| 50 | 1 | — | 3 | 4 | 4 | 3 | 4 | 3 | 3 | 4 | 4 |
| 61 | 0 | 3 | 2 | 3 | 3 | 3 | 4 | 3 | 4 | 4 | 4 |
| 64 | 2 | 4 | 3 | 5 | 5 | 5 | 5 | 5 | 5 | 5 | 5 |
| 79 | 1 | 2 | 3 | 3 | 3 | 4 | 5 | 5 | 5 | 5 | 5 |
| 80 | 1 | 3 | 3 | 2 | 3 | 4 | 5 | 4 | 5 | 5 | 5 |
| 97 | 1 | 2 | 2 | 3 | 3 | 3 | 4 | 5 | 4 | 5 | 5 |

TABLE 8-continued

| Comd. No. | Dose g/ha | Ory | Ane | Ech.o | Sci | Mon | Cyp | Sag | Sag.t | Ele | Pot |
|---|---|---|---|---|---|---|---|---|---|---|---|
| 141 | 1 | 2 | 4 | 4 | 5 | 4 | 5 | 5 | 5 | 5 | 5 |
| 142 | 1 | — | 3 | 5 | 5 | 4 | 4 | 5 | 5 | 5 | 4 |
| 147 | 1 | 2 | 3 | 3 | 3 | 4 | 5 | 4 | 5 | 4 | 5 |
| 176 | 1 | 2 | 3 | 5 | 5 | 4 | 5 | 4 | 5 | 5 | 5 |
| 179 | 0 | 3 | 3 | 5 | 4 | 4 | 5 | 5 | 5 | 5 | 5 |
| 180 | 0 | 5 | 5 | 4 | 5 | 5 | 5 | 5 | 5 | 5 | 5 |
| 184 | 0 | 3 | 4 | 3 | 3 | 4 | 5 | 5 | 4 | 5 | 5 |

We claim:

1. A 6-chloro-2-(4,6-dimethoxypyrimidin-2-yl)oxybenzoic acid imino ester compound of the formula (I):

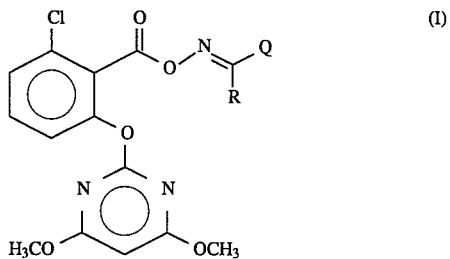

wherein

Q represents a straight or branched alkyl group having from 1 to 10 carbon atoms, a straight or branched alkenyl group having 2 to 10 carbon atoms or a cycloalkyl group having from 3 to 10 carbon atoms, which may be substituted with a $(C_1-C_4)$alkoxy or $(C_1-C_4)$alkylthio group; a $(C_1-C_4)$alkyl or $(C_2-C_4)$alkenylthio group; a phenylthio group; a phenyl$(C_1-C_4)$alkyl or phenyl$C_2-C_4$)alkenylthio group; or a radical of the following formula:

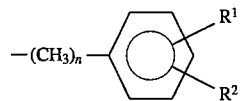

wherein $R^1$ and $R^2$ are the same or different from each other and represent hydrogen or a halogen atom; or a group selected from the groups consisting of a $(C_1-C_4)$alkyl, a $(C_2-C_4)$alkenyl, an acyl, an acyloxy, a $(C_1-C_4)$alkylthio, a nitro, a cyano, a phenyl and a phenoxy group, and which, if necessary, may be substituted with a halogen atom, a $(C_1-C_4)$,alkyl, a $(C_1-C_4)$alkoxy or an acetal group; or $R^1$ and $R^2$ may constitute an acetal structure with carbon atoms to which $R^1$ and $R^2$ are linked; and, n is 0 or 1; $R^1$ and $R^2$ together form 3', 4'-methylenedioxy; and R presents a hydrogen or a halogen atom, a cyano group, or -Z-$R^3$, wherein $R^3$ represents a $(C_1-C_4)$alkyl, an alkoxy group having from 1 to 8 carbon atoms, or an alkenyloxy group having 2 to 8 carbon atoms, or a phenyl, a phenoxy or an amino group, or 5–6 membered hetero or aromatic ring system, which is a phenyl, a furyl, a thienyl, a pyrrolyl or a pyranyl group, connecting to Z through a $(C_1-C_2)$alkyl or alkoxy bridge, which may have one or more proper substituents selected from the group consisting of a halogen atom, a $(C_1-C_4)$alkyl, a hydroxy, a nitro or a cyano group on its certain positions, or in some cases, $R^3$ may be cyclized with Z to form a morpholine or $R^3$ may be cyclized with Z and Q, to form

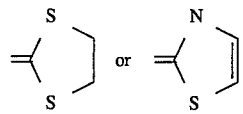

and which may have methyl and/or phenyl substituents; and, Z represents —O—, —S—,

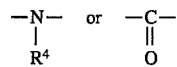

wherein $R^4$ is a hydrogen atom, a $(C_1-C_4)$alkyl or a phenyl group, or constitutes a 5–6 membered cyclic system containing an oxygen atom with $R^3$.

2. The benzoic acid imino ester compound according to claim 1, wherein R is a hydrogen or a halogen atom, a $(C_1-C_4)$alkyl group, a substituted oxy carbonyl group, a $(C_1-C_4)$alkoxy group, a $(C_1-C_4)$alkylthio group, an acyl group, a substituted amino group or a cyano group; and Q is an alkyl group having from 1 to 8 carbon atoms, a phenyl group which may be substituted with a halogen atom, $(C_1-C_4)$alkyl group, halomethyl or $(C_1-C_4)$alkoxy group or a $(C_1-C_4)$alkylamino group.

3. A pyridine mercapto ester of the formula (II):

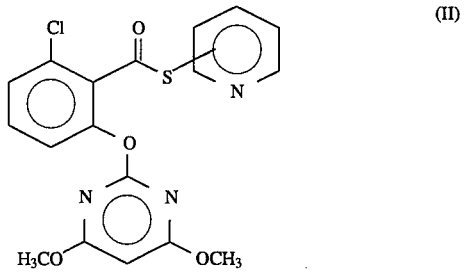

4. A herbicidal composition comprising a herbicidally effective amount of a 6-chloro-2-(4,6-dimethoxypyrimidin-2-yl)oxybenzoic acid imino ester derivative as defined in claim 1 and an agricultural adjuvant.

5. A method for killing weeds which comprises applying a herbicidally effective amount of a 6-chloro-2-(4,6-dimethoxypyrimidin-2-yl)oxybenzoic acid imino ester compound as defined in claim 1 to a locus to be protected.

6. A process of preparing a 6-chloro-2-( 4,6-dimethoxypyrimidin-2-yl)oxybenzoic acid imino ester compound of formula (I):

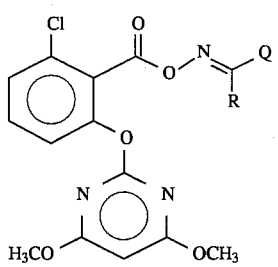

wherein

Q represents a straight or branched alkyl group having from 1 to 10 carbon atoms, a straight or branched alkenyl group having 2 to 10 carbon atoms, or a cycloalkyl group having from 3 to 10 carbon atoms, which may be substituted with a $(C_1-C_4)$alkoxy or $(C_1-C_4)$alkylthio group; a $(C_1-C_4)$alkyl or $(C_2-C_4)$alkenylthio group; a phenylthio group; a phenyl$(C_1-C_4)$alkyl or phenyl$(C_2-C_4)$alkenylthio group; or a radical of the following formula:

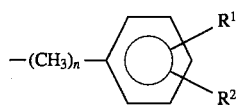

wherein $R^1$ and $R^2$ are the same or different from each other and represent hydrogen or a halogen atom; or a group selected from the groups consisting of a $(C_1-C_4)$alkyl, a $(C_2-C_4)$alkenyl, an acyl, an acyloxy, a $(C_1-C_4)$alkylthio, a nitro, a cyano, a phenyl and a phenoxy group, and which, if necessary, may be substituted with a halogen atom, a $(C_1-C_4)$alkyl, a $(C_1-C_4)$alkoxy or an acetal group; or $R^1$ and $R^2$ may constitute an acetal structure with carbon atoms to which $R^1$ and $R^2$ are linked; and, n is 0 or 1; or $R^1$ and $R^2$ together form 3', 4'-methylenedioxy; and R represents hydrogen or a halogen atom, a cyano group, or -Z-$R^3$, wherein $R^3$ represents a $(C_1-C_4)$alkyl, an alkoxy group having from 1 to 8 carbon atoms, or an alkenyloxy group having 2 to 8 carbon atoms, or a phenyl, a phenoxy or an amino group, or 5–6 membered hetero or aromatic ring system which is a phenyl, a furyl, a thienyl, a pyrrolyl or a pyranyl group, connecting to Z through a $(C_1-C_2)$alkyl or alkoxy bridge, which may have one or more proper substituents selected from the group consisting of a halogen atom, a $(C_1-C_4)$alkyl, a hydroxy, a nitro or a cyano group on its certain positions, or in some cases, $R^3$ may be cyclized with Z to form a morpholine or $R^3$ may be cyclized with Z and Q, to form

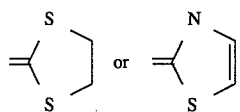

and which may have methyl and/or phenyl substituents; and, Z represents —O—, —S—,

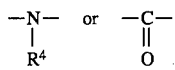

wherein $R^4$ is a hydrogen atom, a $(C_1-C_4)$alkyl or a phenyl group, or constitutes a 5–6 membered cyclic system containing an oxygen atom with $R^3$ which comprises reacting the compound of the following formula (II) and the compound of the following formula (III) in the presence of a solvent

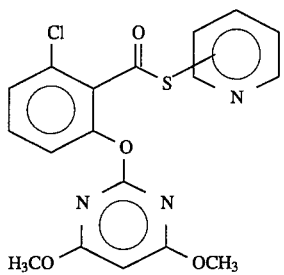

wherein,

R and Q are as defined above.

7. The process according to claim 6, wherein the reaction is conducted in room temperature, and in the presence of copper(II) salt.

8. The process according to claim 6, wherein the solvent is methylene chloride, chloroform, tetrachloromethane,1,2-dichloro ethane, acetonitrile or propionitrile.

9. The benzoic acid imino ester compound according to claim 1, wherein Q has 1 to 8 carbon atoms, providing that if Q is a cycloalkyl group, it has 3 to 8 carbon atoms.

10. The process according to claim 6, wherein Q has 1 to 8 carbon atoms, providing that if Q is a cycloalkyl group, it has 3 to 8 carbon atoms.

11. A 6-chloro-2-(4,6-dimethoxypyrimidin-2-yl)oxybenzoic acid imino ester compound of the formula (I):

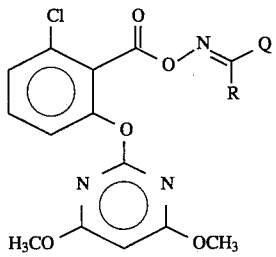

wherein

Q represents a straight or branched alkyl group having from 1 to 10 carbon atoms, a straight or branched alkenyl group having 2 to 10 carbon atoms, or a cycloalkyl group having from 3 to 10 carbon atoms, which may be substituted with a $(C_1-C_4)$alkoxy or $(C_1-C_4)$alkylthio group; a $(C_1-C_4)$alkyl or $(C_2-C_4)$alkenylthio group; a phenylthio group; a phenyl$(C_1-C_4)$alkyl or phenyl$(C_2-C_4)$alkenylthio group; or a radical of the following formula:

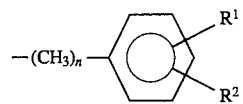

wherein $R^1$ and $R^2$ are the same or different from each other and represent hydrogen or a halogen atom, or a first group selected from the groups consisting of a $(C_1-C_4)$alkyl, a $(C_2-C_4)$alkenyl, an acyl, an acyloxy, a $(C_1-C_4)$alkylthio, a nitro, a cyano, a phenyl and a phenoxy group; or R¹ and R² may constitute an acetal structure with carbon atoms to which R¹ and R² are linked; and, n is 0 or 1; or R¹ and R² together form 3',4'-methylenedioxy; and R represents a hydrogen or a halogen atom, a cyano group, or -Z-R³, wherein R³ represents a $(C_1-C_4)$alkyl group, an alkoxy group having from 1 to 8 carbon atoms, an alkenyloxy group having 2 to 8 carbon atoms, or a phenyl, a phenoxy or an amino group, or a 5–6 membered hetero or aromatic ring system, which is a phenyl, a furyl, a thienyl, a pyrrolyl or a pyranyl group, connecting to Z through a $(C_1-C_2)$alkyl or alkoxy bridge, which may have one or more substituents selected from the group consisting of a halogen atom, a $(C_1-C_4)$alkyl, a hydroxy, a nitro or a cyano group; and, Z represents —O—, —S—,

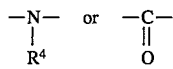

wherein

R⁴ is a hydrogen atom, a $(C_1-C_4)$alkyl or a phenyl group, or a 5–6 membered cyclic system containing an oxygen atom with R³.

12. The benzoic acid imino ester compound according to claim 11, wherein Q has 1 to 8 carbon atoms, providing that if Q is a cycloalkyl group, it has 3 to 8 carbon atoms.

13. A process of preparing a 6-chloro-2-(4,6-dimethoxypyrimidin-2-yl)oxybenzoic acid imino ester compound of formula (I):

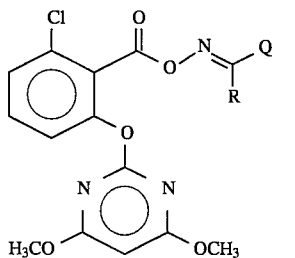

wherein,

Q represents a straight or branched alkyl group having from 1 to 10 carbon atoms, a straight or branched alkenyl group having 2 to 10 carbon atoms or a cycloalkyl group having from 3 to 10 carbon atoms, which may be substituted with a $(C_1-C_4)$alkoxy or $(C_1-C_4)$alkylthio group; a $(C_1-C_4)$alkyl or $(C_2-C_4)$alkenylthio group; a phenylthio group; a phenyl$(C_1-C_4)$alkyl or phenyl$(C_2-C_4)$alkenylthio group; or a radical of the following formula:

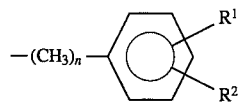

wherein

R¹ and R² are the same or different from each other and represent hydrogen or a halogen atom; or a first group selected from the groups consisting of a $(C_1-C_4)$alkyl, a $(C_2-C_4)$alkenyl, an acyl, an acyloxy, a $(C_1-C_4)$alkylthio, a nitro, a cyano, a phenyl and a phenoxy group; or R¹ and R² may constitute an acetal structure with carbon atoms to which R¹ and R² are linked; and, n is 0 or 1; or R¹ and R² together form 3,40,4'-methylenedioxy; and, R represents a hydrogen or a halogen atom, a cyano group, or -Z-R³, wherein R³ includes a $(C_1-C_4)$alkyl group, an alkoxy group having from 1 to 8 carbon atoms, or an alkenyloxy group having 2 to 8 carbon atoms, or a phenyl, a phenoxy or an amino group, or a 5–6 membered hetero or aromatic ring system, which is a phenyl, a furyl, a thienyl, a pyrrolyl or a pyranyl group, connecting to Z through a $(C_1-C_2)$alkyl or alkoxy bridge, which may have one or more substituents selected from the group consisting of a halogen atom, a $(C_1-C_4)$alkyl, a hydroxy, a nitro or a cyano group; and, Z represents —O—, —S—,

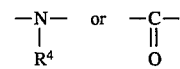

wherein

R⁴ is a hydrogen atom, a $(C_1-C_4)$alkyl or a phenyl group, or a 5–6 membered cyclic system containing an oxygen atom with R³ which comprises reacting the compound of the following formula (II) and the compound of the following formula (III) in the presence of a solvent

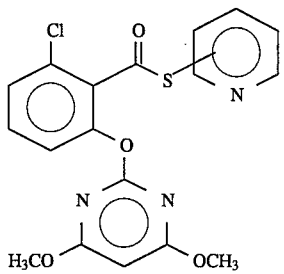

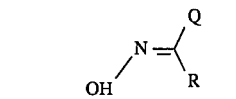

wherein,

R and Q are as defined above.

14. The process according to claim 13, wherein Q has 1 to 8 carbon atoms, providing that if Q is a cycloalkyl group, it has 3 to 8 carbon atoms.

* * * * *